(12) United States Patent
Roh et al.

(10) Patent No.: US 11,957,423 B1
(45) Date of Patent: Apr. 16, 2024

(54) MULTI-ARM SURGICAL ROBOTIC SYSTEM

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael D'Andrea, Burlington, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 18/455,472

(22) Filed: Aug. 24, 2023

Related U.S. Application Data

(63) Continuation of application No. 17/865,342, filed on Jul. 14, 2022, which is a continuation-in-part of application No. 17/408,407, filed on Aug. 21, 2021, now abandoned.

(51) Int. Cl.
| | |
|---|---|
| *A61B 34/30* | (2016.01) |
| *A61B 5/0205* | (2006.01) |
| *A61B 34/00* | (2016.01) |
| *A61B 90/00* | (2016.01) |

(52) U.S. Cl.
CPC ............ *A61B 34/30* (2016.02); *A61B 5/0205* (2013.01); *A61B 34/25* (2016.02); *A61B 34/74* (2016.02); *A61B 90/37* (2016.02); *A61B 2034/252* (2016.02); *A61B 2034/306* (2016.02); *A61B 2034/742* (2016.02); *A61B 2090/376* (2016.02)

(58) Field of Classification Search
CPC ....... A61B 34/30; A61B 5/0205; A61B 34/25; A61B 34/74; A61B 90/37; A61B 2034/252; A61B 2034/306; A61B 2034/742; A61B 2090/376
See application file for complete search history.

(56) References Cited

U.S. PATENT DOCUMENTS

2022/0335604 A1* 10/2022 Vanosdoll ............ G06V 10/764

* cited by examiner

*Primary Examiner* — Basil T. Jos
(74) *Attorney, Agent, or Firm* — Perkins Coie LLP

(57) ABSTRACT

A robotic surgery system comprising a plurality of motorized robotic arms of a surgical robot configured to perform surgical steps on a patient and a display system for multi-user control of the robot of a surgical procedure. The display system includes a console including left and right hand-operated input devices physically manipulatable by a first user and a viewer configured to display one or more instruments carried by the plurality of robotic arms to the second user. The display system also includes a second user device configured to display a graphical user interface having patient data of the patient and an authorization input for a second user to be authorized to switch control of at least one of the robotic arms from the first user to the second user.

8 Claims, 16 Drawing Sheets

500

| Surgical Consultant | Specialty | Rate | Availability | History |
|---|---|---|---|---|
| Jane Doe | ABC Brand Robotics | $2000/procedure | JDSchedule.dat | JDHistory.dat |
| Steve Hanks | Orthopedics | $5000 on-call +$1000 per engagement | SHDSchedule.dat | SHHistory.dat |
| Sue Jones | Anesthesia | $10,000/procedure | SJSchedule.dat | SJHistory.dat |

| Procedure | Surgical Consultant 1 | Engagement status | Surgical Consultant 2 | Engagement status | Procedure status |
|---|---|---|---|---|---|
| Bob Smith right knee replacement | Jane Doe | Accepted | Steve Hanks | Accepted | Settled |
| Mark Stevens appendectomy | Sue Jones | Proposed | NA | | Scheduled |

*FIG. 6*

MULTI-ARM SURGICAL ROBOTIC SYSTEM

CROSS-REFERENCE TO RELATED APPLICATIONS

This application is a continuation of U.S. patent application Ser. No. 17/865,342, filed Jul. 14, 2022, entitled "TELEMETRY-BASED CONTROL OF ROBOTIC SYSTEMS," which is a continuation-in-part of U.S. patent application Ser. No. 17/408,407, filed Aug. 21, 2021, entitled "TELEPRESENCE-BASED SURGICAL CONSULTING," all of which are incorporated herein by reference in their entireties.

TECHNICAL FIELD

The present disclosure is generally related to automated and robotic surgical systems and specifically to systems and methods for surgical suites with remote control of surgical robotics and equipment in surgical suites.

BACKGROUND

More than 200 million surgeries are performed worldwide each year and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and amongst the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the healthcare team. However, conventional methods are typically insufficient to prevent surgical errors and adverse events during surgery.

SUMMARY

Methods, apparatus, and systems for telemetry-based control of robotic surgical systems are disclosed. A remote surgical consulting system allows medical professionals and medical device technicians to remotely engage with surgical staff, patients, and surgical equipment in real-time and identify available consultants to connect to when needed.

In some embodiments, a system for telemetry-based control for a surgical procedure includes a surgical consulting network, a hospital with an operating room for the surgical procedure, a digital assistant interface in the operating room, at least one consultant user device, a database of available consultants, and a database of surgical procedures, wherein at least one consultant user device can be connected to the operating room to allow a remote user to interact with the people or equipment in the operating room for the surgical procedure.

In some embodiments, in response to receiving a prompt indicating a surgical procedure from a computer device at a medical facility, a computer system schedules the surgical procedure based on patient data retrieved from an electronic health records database. The computer system receives a surgical consulting requirement of the medical facility for the surgical procedure. The surgical consulting requirement is received from the computer device. The computer system identifies a surgical consultant from a consultant database based on the surgical consulting requirement. The computer system receives a message that the surgical procedure has been initiated. The computer system establishes a communication channel between the computer device at the medical facility and a consultant user device of the surgical consultant. The communication channel is for the surgical consultant to provide surgical consulting related to the surgical procedure. The computer system determines that the surgical procedure has been completed. In response to determining that the surgical procedure has been completed, the computer system terminates the communication channel.

These and other aspects, features, and implementations can be expressed as methods, apparatus, systems, components, program products, means, or steps for performing a function, and in other ways.

These and other aspects, features, and implementations will become apparent from the following descriptions, including the claims.

BRIEF DESCRIPTION OF THE DRAWINGS

FIG. 5 is a table illustrating an example consultant database, in accordance with one or more embodiments.

FIG. 6 is a table illustrating an example schedule database, in accordance with one or more embodiments.

DETAILED DESCRIPTION

Figure 1:
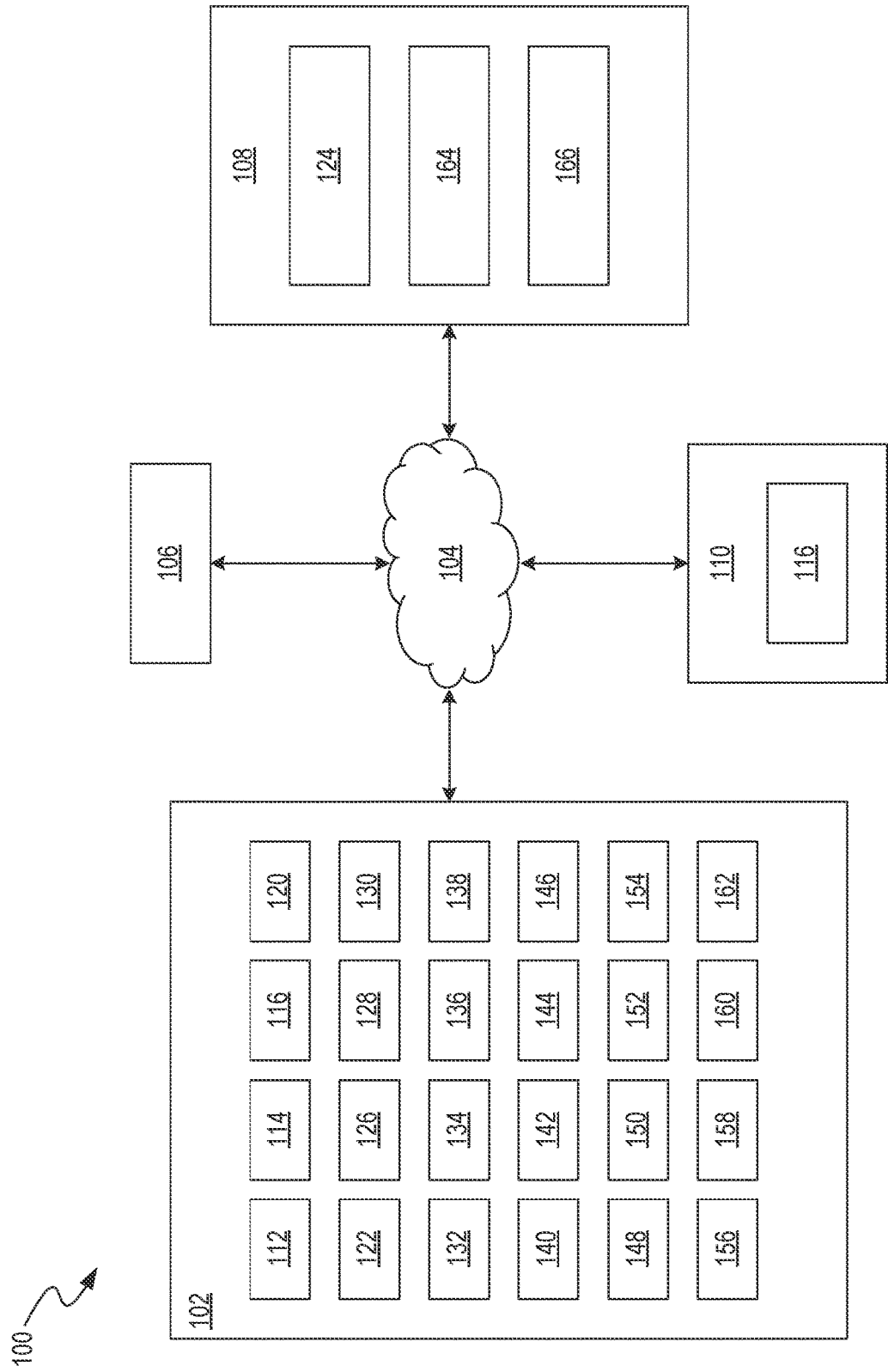
FIG. 1 is a block diagram illustrating an example system for telepresence-based surgical consulting, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples.

Telemedicine can connect medical professionals worldwide and allow for the exchange of ideas and knowledge that can improve patient outcomes. This document presents methods, systems, and apparatus for telemetry-based control of robotic surgical systems. Using the embodiments disclosed herein, a remote surgical consulting system allows medical professionals and medical device technicians to remotely engage with surgical staff, patients, and surgical equipment in real-time and identify available consultants to connect to when needed. The embodiments provide a robotic surgical system to enable remote surgeons to control a surgical robot's actions remotely and provide guidance for professionals on site. The embodiments provide dynamic engagement levels in surgical consulting.

In some embodiments, a system for remote consulting for a surgical procedure includes a surgical consulting network, a hospital with an operating room for the surgical procedure, a digital assistant interface in the operating room, at least one consultant user device, a database of available consultants, and a database of surgical procedures, wherein at least one consultant user device can be connected to the operating room to allow a remote user to interact with the people or equipment in the operating room for the surgical procedure.

The advantages and benefits of the methods, systems, and apparatus for telemetry-based control of robotic surgical systems disclosed herein include compatibility with best practice guidelines for surgery in an operating room, e.g., from regulatory bodies and professional standards organizations such as the Association for Surgical Technologists. The robotic surgery technologies disclosed offer valuable enhancements to medical or surgical processes through improved precision, stability, and dexterity. The disclosed methods relieve medical personnel from routine tasks and make medical procedures safer and less costly for patients. The embodiments disclosed can also perform more accurate surgery and address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers advantages, such as no line of sight required, read multiple radio frequency identification (RFID) objects at once, scan at a distance, and flexibility. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example system 100 for telepresence-based surgical consulting, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The system 100 is implemented using the components of the example computer system 300 illustrated and described in more detail with reference to FIG. 3. Likewise, embodiments of the system 100 can include different and/or additional components, or be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide (referred to as end tidal carbon dioxide, ETCO2) that is released at the end of an exhaled breath. An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and sensorimotor cortex, which help in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals elicited by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limb, lower limb, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of target site such as pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end-effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors comprise a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or light-emitting diodes (LEDs). Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and is widely used can be procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of tool-tissue interaction forces. During MIS, the field of view and workspace of tools are compromised due to the indirect access to the anatomy and lack of surgeon's hand-eye coordination. The sensors 134 provide a tactile sensation to the surgeon by providing information of shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can more widely suit for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"— of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location of where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient as well as filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform, flex, or extend individual components of the platform, or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a postoperative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions which are suitable for operation; protect patient from being chilled; and be prepared to meet any emergency.

In some embodiments, the system 100 includes a Jackson frame 144 (or Jackson table), which refers to a frame or table which is designed for use in spine surgeries and can be used in a variety of spinal procedures in supine, prone, or lateral positions in a safe manner. Two peculiar features of the Jackson table 144 are no central table support and an ability to rotate the table through 180 degrees. The Jackson table 144 is supported at both ends which keeps the whole of the table free. This allows the visualization of trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (also referred to as a Bair). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter. High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot and ankle, shoulder and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a tool designed to gradually correct a deformity, e.g., corsets, splints, orthopedic footwear, insoles, and other devices to correct abnormal positions of the foot. A compression-distraction tool refers to a tool designed to correct acquired or congenital deformities of the extremities, e.g., curvature, shortening, and pseudarthrosis such as Gudushauri. A fixation tool can be an internal fixation tool (e.g., screws, plates) or external fixation tool (for the radius, tibia fracture fixation). The orthopedic tools can be bone-holding forceps, drill bits, nail pins, hammer, staple, etc.

In some embodiments, the tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can comprise a physical drill, power cord, electronically motorized bone drill, or rotating bone shearing incision work unit.

In some embodiments, the tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on material synthetic and natural. Stitches can be based on coating coated and un-coated.

In some embodiments, the tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. The ventilator is required when a person is not able to breathe on their own. The ventilator can perform a function of gently pushing air into the lungs (like lungs when they are working) and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can comprise a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment 102. The consumables 158 can include gloves, gowns, masks, syringes, needles, sutures, staples, tubing, catheters, or adhesives for wound dressing, in addition to other tools needed by doctors and nurses to provide care. Depending on the device, mechanical testing can be carried out in tensile, compression or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, used to tag an instrument with an electronic tag and tracks it using the tag. Typically, this could involve a centralized platform that provides details such as location, owner, contract, and maintenance history for all equipment in real-time. A variety of techniques can be used to track physical assets, including radio frequency identification (RFID), global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. RFID can be very short for low frequency, high frequency, or ultra-high frequency. Managing and locating important assets is a key challenge for tracking medical equipment. Time spent searching for critical equipment can lead to expensive delays or downtime, missed deadlines and customer commitments, and wasted labor. The problem has been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light illuminated and the image seen with the microscope 116 is two-dimensional), dissection or stereoscope (light illuminated and image seen with the microscope 116 is three-dimensional), confocal (laser-illuminated and image seen with the microscope 116 is on a digital computer screen), scanning electron (SEM) (electron illuminated and image seen with the microscope 116 is in black and white), or transmission electron microscope (TEM) (electron illuminated and image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EH R 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In some embodiments, the system 100 or the console 108 uses quantum computing. Quantum computing refers to a computational device or method that utilizes properties of quantum states defined by quantum mechanics such as superposition, entanglement, etc., to perform computations. Quantum devices utilize qubits which are the quantum equivalent to bits in a classical computing system. Qubits include at least two quantum states or probable outcomes. These outcomes, combined with a coefficient representing the probability of each outcome, describe the possible states, or bits of data, which can be represented by the qubits according to the principle of quantum superposition. These states can be manipulated which can shift the probability of each outcome or additionally add additional possible outcomes to perform a calculation, the final state of which can be measured to achieve a result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows great promise for drug discovery and simulating the interaction of drugs with biologic systems, however, the same technology can be used to predict the interaction of a biologic system with an implanted device, preventing rejection of an implant by a patient's body, long term function of an implant, and potentially the reaction of a patient to a surgical procedure during a simulation before a procedure or actively during a procedure.

Figure 2:
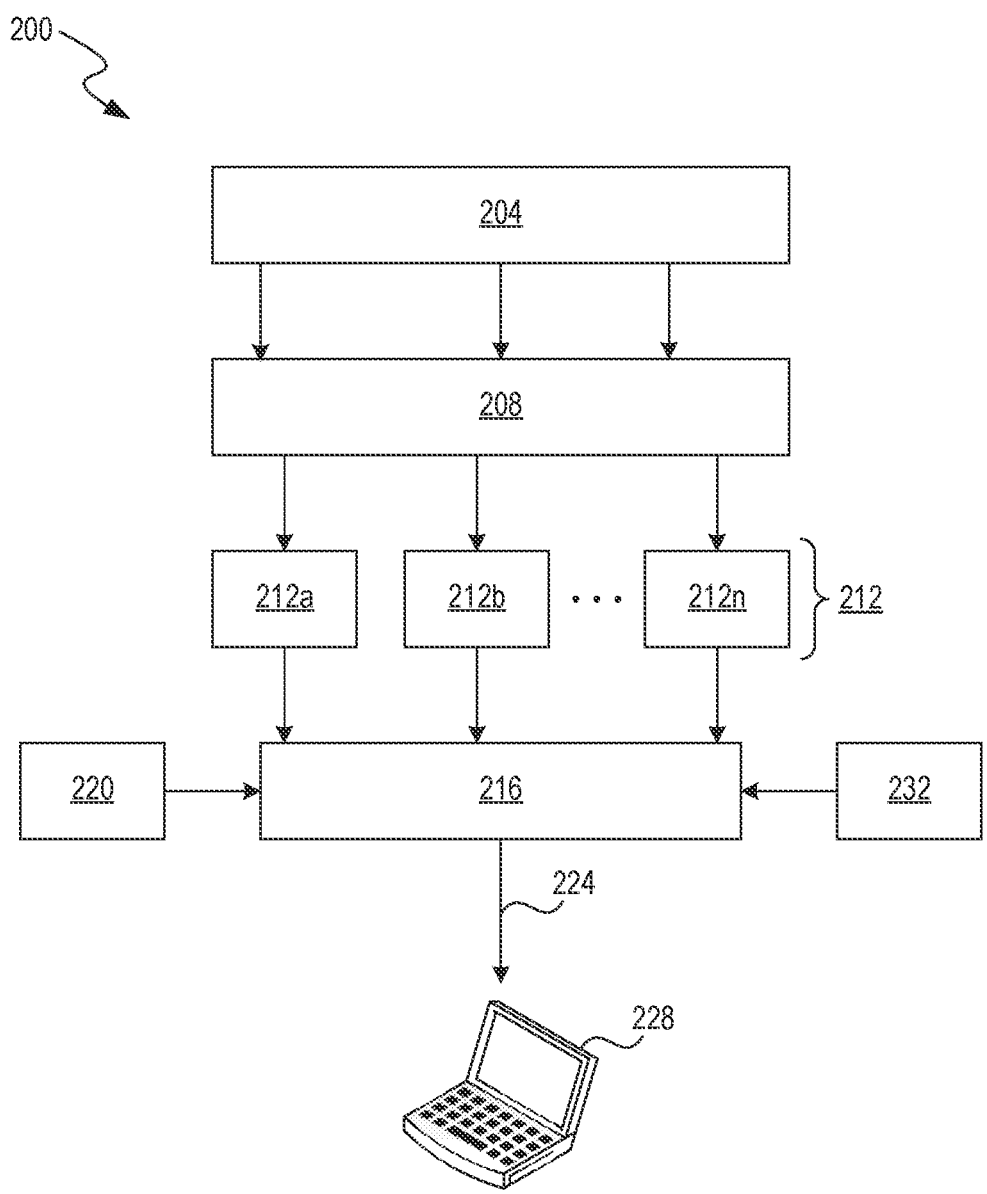
FIG. 2 is a block diagram illustrating an example machine learning system for telepresence-based surgical consulting, in accordance with one or more embodiments.

FIG. 2 is a block diagram illustrating an example machine learning system 200 for telepresence-based surgical consulting, in accordance with one or more embodiments. The machine learning system 200 is implemented using components of the example computer system 300 illustrated and described in more detail with reference to FIG. 3. For example, the machine learning system 200 can be implemented on the console 108 using instructions programmed in the memory 164 illustrated and described in more detail with reference to FIG. 1. Likewise, embodiments of the machine learning system 200 can include different and/or additional components, or be connected in different ways. The machine learning system 200 is sometimes referred to as a machine learning module.

The machine learning system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., feature 212a, feature 212b, and feature 212n. The feature vector 212 contains the relevant information from the input data 204, such that events or data value thresholds of interest can be identified by the machine learning model 216 by using this reduced representation. In some example embodiments, the following dimensionality reduction techniques are used by the feature extraction module 208: independent component analysis, Isomap, Kernel PCA, latent semantic analysis, partial least squares, principal component analysis, multifactor dimensionality reduction, nonlinear dimensionality reduction, Multilinear Principal Component Analysis, multilinear subspace learning, semidefinite embedding, autoencoder, and deep feature synthesis.

In alternate embodiments, the machine learning model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the machine learning system 200. For example, the machine learning model 216 can use a cascade of multiple layers of nonlinear processing units for implicit feature extraction and transformation. Each successive layer uses the output from the previous layer as input. The machine learning model 216 can thus learn in supervised (e.g., classification) and/or unsupervised (e.g., pattern analysis) modes. The machine learning model 216 can learn multiple levels of representations that correspond to different levels of abstraction, wherein the different levels form a hierarchy of concepts. In this manner, the machine learning model 216 can be configured to differentiate features of interest from background features.

In alternative example embodiments, the machine learning model 216, e.g., in the form of a convolutional neural network (CNN) generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the machine learning system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The machine learning model 216 can be a CNN that includes both convolutional layers and max pooling layers. The architecture of the machine learning model 216 can be "fully convolutional," which means that variable sized sensor data vectors can be fed into it. For all convolutional layers, the machine learning model 216 can specify a kernel size, a stride of the convolution, and an amount of zero padding applied to the input of that layer. For the pooling layers, the model 216 can specify the kernel size and stride of the pooling.

In some embodiments, the machine learning system 200 trains the machine learning model 216, based on the training data 220, to correlate the feature vector 212 to expected outputs in the training data 220. As part of the training of the machine learning model 216, the machine learning system 200 forms a training set of features and training labels by identifying a positive training set of features that have been determined to have a desired property in question, and, in some embodiments, forms a negative training set of features that lack the property in question.

The machine learning system 200 applies machine learning techniques to train the machine learning model 216, that when applied to the feature vector 212, outputs indications of whether the feature vector 212 has an associated desired property or properties, such as a probability that the feature vector 212 has a particular Boolean property, or an estimated value of a scalar property. The machine learning system 200 can further apply dimensionality reduction (e.g., via linear discriminant analysis (LDA), principle component analysis (PCA), or the like) to reduce the amount of data in the feature vector 212 to a smaller, more representative set of data.

The machine learning system 200 can use supervised machine learning to train the machine learning model 216, with feature vectors of the positive training set and the negative training set serving as the inputs. In some embodiments, different machine learning techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The machine learning system 200 applies the trained machine learning model 216 to the features of the validation set 232 to quantify the accuracy of the machine learning model 216. Common metrics applied in accuracy measurement include: Precision and Recall, where Precision refers to a number of results the machine learning model 216 correctly predicted out of the total it predicted, and Recall is a number of results the machine learning model 216 correctly predicted out of the total number of features that had the desired property in question. In some embodiments, the machine learning system 200 iteratively re-trains the machine learning model 216 until the occurrence of a stopping condition, such as the accuracy measurement indication that the machine learning model 216 is sufficiently accurate, or a number of training rounds having taken place.

Figure 3:
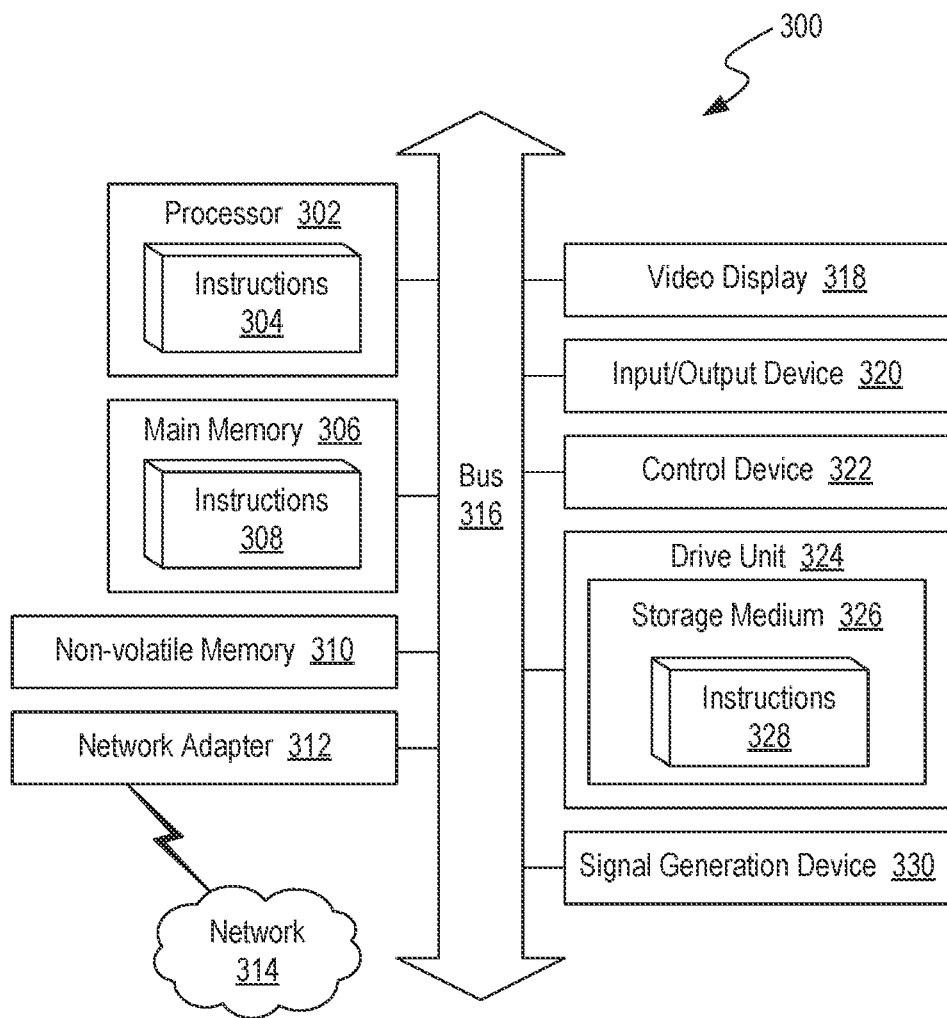
FIG. 3 is a block diagram illustrating an example computer system for telepresence-based surgical consulting, in accordance with one or more embodiments.

FIG. 3 is a block diagram illustrating an example computer system for telepresence-based surgical consulting, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the machine learning system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include, for example, a firewall or other feature that governs and/or manages permission to access proxy data in a computer network and/or tracks varying levels of trust between different machines and/or applications. The firewall can be any number of modules having any combination of hardware and/or software components able to enforce a predetermined set of access rights between a particular set of machines and applications, machines and machines, components of machines, and/or applications and applications (e.g., to regulate the flow of traffic and resource sharing between these entities). The firewall can additionally manage and/or have access to an access control list that details permissions including the data rights, access rights, and/or operation rights of an object by an individual, a machine, and/or an application, and the circumstances (e.g., adverse event, deviation from procedure or surgical plan, network communication failure, surgical procedure progress within predicted range, etc.) under which the permission rights stand.

The computer system 300 can dynamically manage one or more consultants by analyzing a procedure plan to determine permissions for each of the consultants based on surgical steps to be performed. The computer system 300 can schedule permissions events (e.g., granting, modification, and/or revocation of permissions) and then coordinate permissions according to, for example, network capabilities, procedure safety and/or outcome settings, etc. For surgical robots, the permissions can be specific for one or more instruments, end effectors, arms, etc. The computer system 300 can provide control of different components of the surgical robots to different consultants according to a procedure plan, consultant requests, surgical team requests, etc. The procedure plan can include a surgical plan, a patient monitoring plan, and/or other plans disclosed herein.

The network adapter 312 can provide access management (e.g., remote access) to machines or applications such that when a portion of the procedure assigned to a consultant has been completed, the system can automatically terminate that consultant's access/control. This prevents the same medical equipment from being operated by, or prevents an attempt being made to operate the same medical equipment by, multiple consultants. The network adapter 312 can manage authorization, permission, and/or access (e.g., operating a machine or a component of medical equipment, read-only capability of a machine/application, editing capability of a surgical plan, privacy protecting, etc.) to the machines or applications based on geolocation of the user, biometrics, user credentials, blockchain, token, and/or key functionality for user authentication. For example, the network adapter 312 can provide token functionality for user authentication to access/control the machines or applications. The network adapter 312 can generate a token for the user to access/control a machine or application. In some implementations, the token is valid for a threshold of time, surgical session, and/or surgical step(s) during which the user can access/control the machine or application. For example, a surgeon can access/control a machine or application during a time of a surgery (or a period of the surgery) but is unable to access/control the machine outside of the surgery time. The network adapter 312 can concurrently manage tokens for any number of consultants or other users before and/or during a surgical procedure.

In some implementations, the network adapter 312 provides a user access to a particular machine, component of a machine, or application but restricts the user from accessing other machines, components of machines, or applications. For example, an anesthesiologist can be granted access/control to a machine or application that is related to anesthesiology, such as machines or applications that monitor and control the patient's vital life functions. This allows the anesthesiologist to control operation of machines in real-time (or near-real-time). However, the network adapter 312 does not provide the anesthesiologist access to operate machines (e.g., surgical robotics for orthopedic procedures) and/or applications not related to anesthesiology. The network adapter 312 can allow other consultants with read-only or access data-only rights to receive data from the machines to monitor the patient without allowing concurrent control by multiple consultants. Multiple consultants can view data (e.g., patient data, machine operation data, etc.) while avoiding multiple users attempting to control the same machine. Permissions and/or rights can be granted for a surgical procedure or portion thereof. In some embodiments, permissions and/or rights can be granted for entire surgical procedures, surgical step(s) (e.g., a sequence of surgical steps), completion of a step, etc. The computer system 300 can determine permissions using one or more machine learning algorithms to provide access to perform responsibilities, plan for potential adverse events, etc.

A user can request and receive a token from the network adapter 312 to access a machine or application. In some implementations, the network adapter 312 provides key functionality for the user to access the machine or application. The network adapter 312 can share an authentication key (e.g., symmetric or asymmetric key) with the user over a secure channel for the user to access/control a machine or application. In some procedures, the user can be a remote consultant that requests a token prior to beginning a surgical procedure. The authentication process can be completed to confirm that the consultant will be able to participate in a surgical procedure. In some procedures, the user can request a token during the surgical procedure. For example, the consultant can be notified to participate after beginning the surgical procedure. The consultant can then request a token from the network adapter 312. The authentication process can be performed while the surgical procedure continues. This allows new consultants to be invited to and authenticated during a surgical procedure.

The network adapter 312 can provide biometric functionality for a user to access a machine or application. A user can provide their biometric information (e.g., voice, facial scan, fingerprint, iris scanning, dental records, height, weight, etc.) to the network adapter 312. The network adapter 312 can store the biometric information. When the user requests access, the network adapter 312 can verify the identity of the user based on the biometric information before granting the user access to control, for example, a machine or application. The consultant device can include a biometric input (e.g., camera, fingerprint scanner, iris scanner, etc.) for obtaining biometric information.

The network adapter 312 can provide or support geolocation functionality for user authentication to remotely access and control a machine or application. The network adapter 312 can verify the location of the user device requesting to access/control a machine or application when determining to permit a user to remotely access/control a machine or application. In an example, a healthcare provider can only access/control a machine or application at a healthcare facility, a surgical suite, etc.

The network adapter 312 can authenticate a user to access one or more machines or applications with a multi-factor identification, such as requiring two types of authentication from an authentication group, which includes blockchain, biometric, token, key, and geolocation types of authentication. The network adapter 312 can adjust the authentication requirements based on a patient's data/vitals, such as health metrics. For example, if the patient's heart rate is below a threshold level (e.g., indicating the user is experiencing a medical emergency), the network adapter 312 requires lower levels of authentication or no authentication for a healthcare provider to remotely access and control a machine or application. Adjusting the level of authentication allows healthcare providers (e.g., surgeon, EMT, etc.) to access/control machines or applications not normally available to them so that they can treat a patient during the medical emergency (e.g., an adverse event). In other implementations, if the patient's heart rate is below the threshold level, the network adapter 312 requires higher levels of authentication for a healthcare provider to remotely access and control a machine or application. The on-site physicians, nurses, and surgical staff can take over operation of previously remote-controlled equipment. Once the patient is stable, based on a confidence of accuracy score above a threshold value, the system can re-establish the telemedicine session with the remote consultant. Increasing the level of authentication allows healthcare providers in the surgical suite to take over control of machines or applications because they have access to additional in-room data and in-person (direct) viewing of the patient.

The network adapter 312 can be incorporated into various components of surgical systems. The location and capabilities of the network adapter 312 can be selected based on the equipment and/or machines located in the surgical room. Multiple network adapters can be incorporated into the computer system 300 and other systems disclosed herein to provide independent management of consultants. A controller (e.g., controller or data system of the surgical robot discussed in connection with FIG. 14A) can include the network adapter (e.g., network adapter 312) to manage multi-consultant control of individual arms and/or end effectors of surgical robots.

Figure 4:
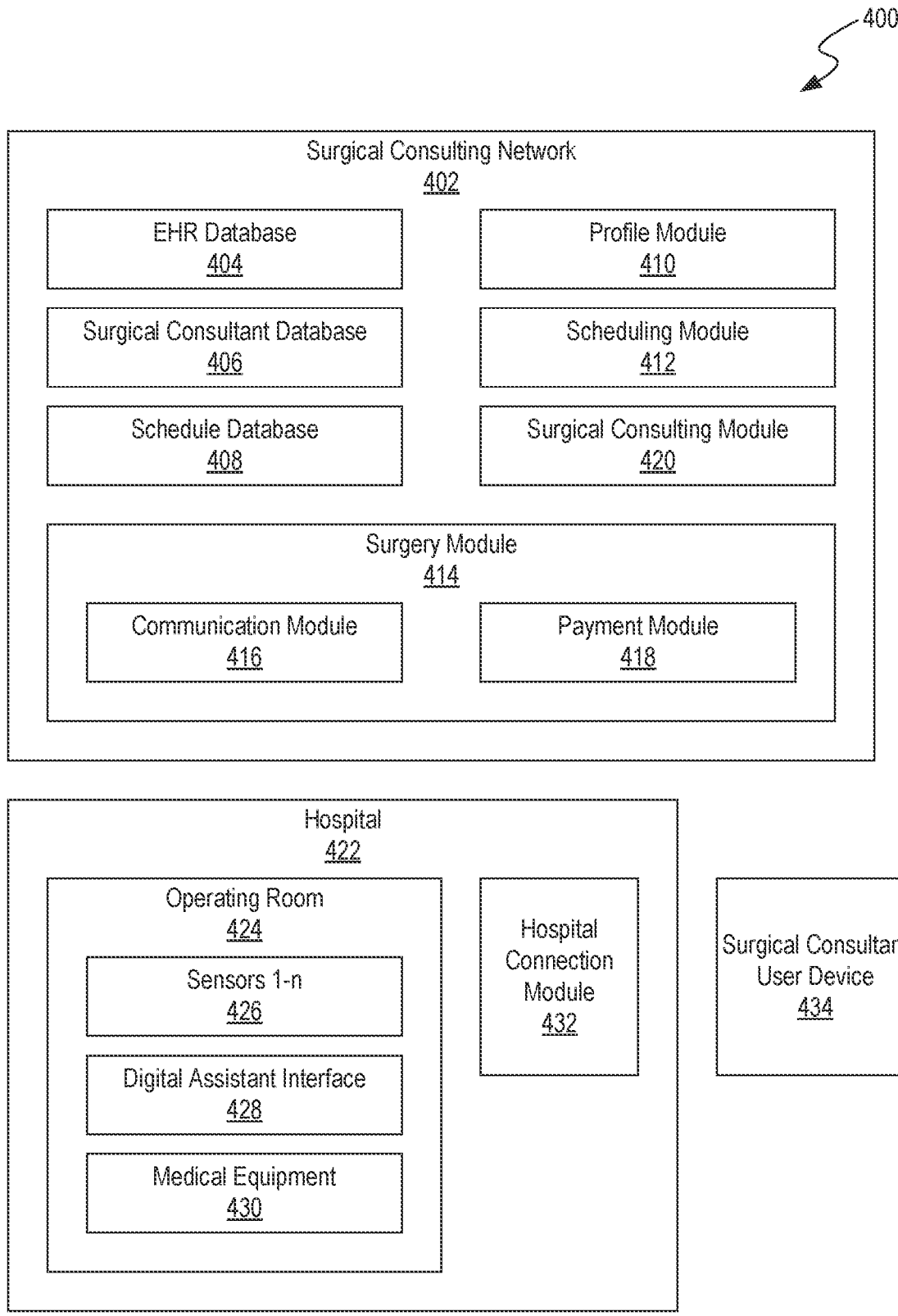
FIG. 4 is a block diagram illustrating an example system for telepresence-based surgical consulting, in accordance with one or more embodiments.

FIG. 4 is a block diagram illustrating an example environment 400 for telepresence-based surgical consulting, in accordance with one or more embodiments. In the environment 400, medical professionals and medical device technicians can remotely engage with surgical staff, patients, or surgical equipment in real-time and identify available consultants to connect to when needed. The system 400 includes a surgical consulting network 402 that connects one or more consultant user devices 434 to one or more hospitals 422. The surgical consulting network 402 is a computer device, such as a server, computer, or tablet, etc., implemented using components of the example computer system 300 illustrated and described in more detail with reference to FIG. 3. In some embodiments, the surgical consulting network 402 is the same as or similar to the console 108 illustrated and described in more detail with reference to FIG. 1. The consultant user devices 434 are computer devices, such as computers or tablets, etc., implemented using components of the example computer system 300 illustrated and described in more detail with reference to FIG. 3. In some embodiments, a consultant user device 434 is the same as or similar to the console 108 illustrated and described in more detail with reference to FIG. 1. Likewise, embodiments can include different and/or additional components, or the components can be connected in different orders.

The environment 400 implements telemetry-based control of a robotic surgical system. Telemetry refers to the in situ collection of measurements, signals, or other data at remote points and their automatic transmission to receiving equipment. Telemetry can be implemented using wireless data transfer mechanisms (e.g., using radio, ultrasonic, or infrared systems) or data transferred over other media such as a telephone or computer network, optical link, or other wired communications, such as power line carriers. In embodiments, the telemetry mechanisms disclosed herein use GSM networks to receive and transmit data, sensors, transmission paths, and display, recording, or control devices. The electronic devices used can be wireless or hard-wired, analog or digital. Other technologies are also possible, such as mechanical, hydraulic, and optical. The telemetry can be commutated to allow the transmission of multiple data streams in a fixed frame.

The consultant user device 434 can be at a remote location (e.g., in another country, state, etc.) from the surgical suite and can communicate with surgical suite machines via one or more networks. For example, the consultant user device 434 can communicate with a surgical suite via a network, such as a wide area network, a cellular network, etc. One or more local networks at the hospital can establish communication channels between pieces of surgical equipment within the surgical suite.

In some embodiments, the surgical consulting network 402 includes an EHR database 404 that stores patient records. The EHR database 404 is the same as or similar to the EHR database 106 illustrated and described in more detail with reference to FIG. 1. Electronic health records are a digital version of patient paper charts. The EHR database 404 can store more information than a traditional patient chart, including but not limited to, patient medical history, diagnoses, medications, treatment plans, allergies, diagnostic imaging, lab results, etc. In some embodiments, the surgical steps for each surgical procedure implemented according to the embodiments disclosed herein are stored in the EHR database 404. The electronic health records can also include data collected from the sensors 426 from historical surgical procedures. The sensors 426 are the same as or similar to the monitors 112 and the sensors 134 illustrated and described in more detail with reference to FIG. 1.

In some embodiments, the surgical consulting network 402 includes a consultant database 406. The consultant database 406 is implemented using components of the example computer system 300 illustrated and described in more detail with reference to FIG. 3. The consultant database 406 stores profiles for surgical consultants that use the surgical consulting network 402. The surgical consultants can be medical practitioners, such as surgeons and anesthesiologists, medical equipment technicians, or medical students or professionals observing a procedure. The information related to the surgical consultants can include contact information, financial account information, medical or equipment specialties, availability, services offered, desired compensation rates, medical facility, educational institution affiliation, etc. In some embodiments, a new profile of a new surgical consultant is generated based on information received describing medical experience of the new surgical consultant. The new profile is stored in the consultant database 406.

A surgical consultant's engagement history can also be stored in the consultant database 406. The engagement history can include the surgical procedures they consulted on, along with details of their involvement in those surgical procedures. In some embodiments, a surgical consulting requirement of a medical facility for a surgical procedure is received from a computer device at the medical facility. The surgical consulting requirement can describe the medical equipment 430 located in the medical facility for performing the surgical procedure. In some embodiments, the engagement history of a surgical consultant who is an anesthesiologist includes each adjustment the consultant made to a piece of medical equipment 430, such as an anesthesiology machine 430. The medical equipment 430 is the same as or similar to the monitors 112 or the equipment 136 illustrated and described in more detail with reference to FIG. 1. The anesthesiology machine 140 is illustrated and described in more detail with reference to FIG. 1. In some embodiments, the consultant database 406 stores surgical procedure context details such as a patient's physiological monitoring data from the one or more sensors 426.

In some embodiments, the surgical consulting network 402 includes a schedule database 408. The schedule database 408 is implemented using components of the example computer system 300 illustrated and described in more detail with reference to FIG. 3. The schedule database 408 can store a schedule related to surgical procedures being performed at a hospital 422 or other medical facilities connected to the surgical consulting network 402 that have an engagement with one or more surgical consultants scheduled or needed. In some embodiments, it is determined that a connection between the consultant user device 434 and the medical equipment 430 at a medical facility is required for the surgical procedure based on engagement information. The connection is implemented using the network adapter 312 and the network 314. A data feed is initiated on a sensor 426 and the medical equipment 430 at the medical facility, in response to determining that the connection is required. The data related to a surgical procedure can include the type of surgical procedure, the medical equipment 430 being used, the surgical consulting role(s), and related compensation rates.

In some embodiments, the surgical consulting network 402 includes a profile module 410. The profile module 410 is implemented using components of the example computer system 300 illustrated and described in more detail with reference to FIG. 3. The profile module 410 enables surgical consultants to create and edit their profiles in the consultant database 406. The surgical consultants can connect their consultant user device(s) 434 to the surgical consulting network 402. The surgical consultants can view, accept, decline, or counter surgical consulting proposals from the hospitals 422 or other medical facilities. In some embodiments, the surgical consulting network 402 includes a scheduling module 412. The scheduling module 412 is implemented using components of the example computer system 300 illustrated and described in more detail with reference to FIG. 3. In some embodiments, in response to receiving a prompt indicating a surgical procedure from a computer device at a medical facility, the scheduling module 412 schedules the surgical procedure based on patient data retrieved from the EHR 404 database. For example, the scheduling module 412 enables users at the hospitals 422 or other medical facilities to add or edit surgical procedures and the details of surgical consulting engagements related to those procedures in the schedule database 408. In some embodiments, engagement information is sent to the consultant user device 434 notifying a surgical consultant of a surgical procedure, in response to identifying the surgical consultant.

In some embodiments, the surgical consulting network 402 includes a surgery module 414. The surgery module 414 is implemented using components of the example computer system 300 illustrated and described in more detail with reference to FIG. 3. In some embodiments, a message is received that the surgical procedure has been initiated. The message can be a text message, an audible alert, a digital signal, an image displayed on a screen, etc., that the surgery module 414 can receive and act upon. The surgery module 414 enables surgical consultants to interact with a surgical procedure in the operating room 424. The operating room 424 is the same as or similar to the operating room 102 illustrated and described in more detail with reference to FIG. 1.

In some embodiments, a communication channel is established between a computer device at a medical facility and the consultant user device 434 of a surgical consultant. The communication channel is for the surgical consultant to provide surgical consulting related to a surgical procedure. The communication is a link over which text, audio, or video is transmitted. The communication channel is implemented using the network 314 and the network adapter 312 illustrated and described in more detail with reference to FIG. 3. In some embodiments, the surgical consultants are a group of medical students observing the surgical procedure through a video feed using the surgery module 414. The surgical consultant can be an anesthesiologist remotely monitoring and controlling the medical equipment 430, such as an anesthesiology machine in some embodiments using the surgery module 414. In some embodiments, the surgical consultant is a surgeon scheduled in advance to observe and provide medical advice related to the present surgical procedure using the surgery module 414.

In some embodiments, the system determines that a surgical procedure has been completed. In response to determining that the surgical procedure has been completed, the communication channel is terminated to, for example, increase available network resources for other communications, prevent unauthorized telepresence by the consultant, eliminate concurrent control of the same equipment by multiple users, and combinations thereof. The termination of the communication channel can be scheduled based on a procedure plan, on-site healthcare workers, etc. The surgery module 414 can also enable unscheduled surgical consultants to be brought in when called for. For example, surgical consultants in various specialties can have on-call hours scheduled using the surgery module 414. In some embodiments, the surgery module 414 includes a communication module 416 implemented using components of the example computer system 300 illustrated and described in more detail with reference to FIG. 3. The communication module 416 is prompted for either scheduled surgical consulting or on-call surgical consulting connections between the operating room 424 and one or more consultant user devices 434. The prompt is a message, such as a text message, audible alert, digital signal, image displayed on a screen, etc., that the communication module 416 can receive and act upon.

In some embodiments, the surgery module 414 includes a payment module 418 implemented using components of the example computer system 300 illustrated and described in more detail with reference to FIG. 3. When a given surgical procedure is complete, the payment module 418 is prompted to determine the compensation due to the surgical consultant based on the surgical consulting engagement and activity during the surgical procedure. The prompt is a message, such as a text message, audible alert, digital signal, image displayed on a screen, etc., that the payment module 418 can receive and act upon. In some embodiments, the communication module 416 enables one or more consultant user devices 434 to connect to one or more sensors 426, a digital assistant interface 428, or the medical equipment 430 in the operating room 424 based on the terms of a surgical consulting engagement and the needs of the operating room 424 team of practitioners. The digital assistant interface 428 can be a computer device, such as a computer or tablet and is implemented using components of the example computer system 300 illustrated and described in more detail with reference to FIG. 3. In some embodiments, the digital assistant interface 428 is a smart assistant or software running on a computer device.

The medical practitioners in an operating room team include surgeons, nurses, technicians, anesthesiologists, etc. The communication module 416 enables the surgical consultants to provide inputs such as voice or text recommendations, questions, or medical equipment 430 adjustments. The communication module 416 can also enable the medical practitioners to indicate the need for an on-call surgical consultant to be brought in by the surgery module 414. In some embodiments, the payment module 418 enables surgical consultants to have their account balances in the consultant database 406 based on their activity in, and terms of, their surgical consulting engagement related to the present surgical procedure. For example, a surgeon brought in to consult on a surgical procedure can be paid a flat rate for their engagement, with additional compensation based on the level they need to be involved with either providing medical guidance or direct control of surgical procedure steps. In some embodiments, the surgical consulting network 402 includes a surgical consulting module 420. The surgical consulting module 420 is implemented using components of the example computer system 300 illustrated and described in more detail with reference to FIG. 3. In some embodiments, the surgical consulting module 420 enables surgical consultants to interact with the profile module 410 and the communication module 418 through their consultant user devices 434.

The hospital 422 and other medical facilities are host to surgical or medical procedures. Each hospital 422 has an account in the schedule database 408 including scheduled surgical procedures, surgical consulting engagements, rates, etc. For surgical procedures, a sterile field is required. In some embodiments, the sterile field maintained in the operating room 424 is in a medical care facility such as the hospital 422, a doctor's office 110, or an outpatient surgery center. The doctor's office 110 is illustrated and described in more detail with reference to FIG. 1.

The operating room 424 can contain some number 1 through n of sensors 426. The sensors 426 are the same as or similar to the monitors 112 and the sensors 134 illustrated and described in more detail with reference to FIG. 1. The sensors 126 can be microphones or optical sensors that generate images or video captured from at least one of multiple imaging devices, such as, cameras attached to manipulators or end-effectors. The manipulators and end-effectors are part of the robotic surgery system 160 illustrated and described in more detail with reference to FIG. 1. In some embodiments, cameras are mounted to the ceiling or other surface above the surgical theater, cameras are mounted on a tripod or other independent mounting device, or cameras are body worn by a surgeon or other surgical staff. In some embodiments, cameras are incorporated into a wearable device, such as an augmented reality device like Google Glass, cameras are integrated to an endoscopic, microscopic, laparoscopic, or any camera or other imaging device (e.g., ultrasound) that is present in the surgical theater, or cameras are associated with one or more areas in the operating room 424.

The sensors 426 are associated with measuring a specific parameter of a patient, such as respiratory rate, blood pressure, blood oxygen level, heart rate, etc. In some embodiments, the operating room 424 includes a digital assistant interface 428. The digital assistant interface 428 is or can execute a digital assistant or other artificial intelligence-based interactive software. The digital assistant interface 428 can display its results on several different computer devices, such as a computer, smartphone, tablet, smart TV, smart speaker, etc. In some embodiments, input is received from the consultant user device 434. The input is related to a surgical procedure. In response to receiving the input, a notification of the input is sent to the digital assistant interface 428 at a medical facility over a communication channel. In some embodiments, information is sent describing an adjustment to the medical equipment 430 at the medical facility, in response to receiving the input.

In some embodiments, the medical equipment 430 used in a surgical procedure is an anesthesiology machine or a robotic surgical tool. In some embodiments, a hospital connection module 432 enables designated users, such as surgeons or administrators, to access the scheduling module 412 to add or edit surgical procedures and their related surgical consulting engagements. The hospital connection module 432 can be software or a computer device implemented using components of the example computer system 300 illustrated and described in more detail with reference to FIG. 3. In some embodiments, the hospital connection module 432 enables designated users, such as surgeons or administrators, to access the surgery module 414 to perform surgical procedures with at least one connected consultant user device 434. In some embodiments, the one or more consultant user devices 434, such as computers, smartphones, tablets, etc., connect to the surgical consulting network 402, interface with the profile module 410, or engage with a surgical procedure using the communication module 416.

In some additional embodiments, at least one communication channel is configured to enable the surgical consultant to interact, via the consultant user device 434, with one or more personnel in the operating room 424 or medical equipment 430 in the operating room 424. The surgical consulting requirement specifies at least one of a surgical plan for the surgical procedure or the medical equipment 430 located in the medical facility for performing the surgical procedure. In some embodiments, the at least one communication channel includes a first communication channel for communication between the surgical consultant and the one or more personnel. The one or more personnel are associated with the surgical procedure. The first communication channel is implemented using the components of the example computer system 300 illustrated and described in more detail with reference to FIG. 3, and especially, the network adapter 312 and the network 314. In some embodiments, the at least one communication channel includes a second communication channel for communication between the surgical consultant and medical equipment for the surgical procedure. The second communication channel provides control of the medical equipment 430 using the consultant user device 434. The second communication channel is implemented using the components of the example computer system 300 illustrated and described in more detail with reference to FIG. 3, and especially, the network adapter 312 and the network 314.

In some embodiments, the surgical consulting network 402 identifies an available surgical consultant for a surgical procedure to be performed in the operating room 424. The surgical consultant is identified from the consultant database 406. The surgical consulting network 402 receives a surgical procedure prompt for a patient. In response to receiving the surgical procedure prompt, the surgical consulting network 402 establishes at least one communication channel between at least one computer device (e.g., the digital assistant interface 428) in the operating room 424 and a remote consultant device 434 of the surgical consultant. The surgical consulting network 402 sends, via the at least one communication channel, patient data of the patient from the operating room 424 to the remote consultant device 434 for viewing by the surgical consultant. The surgical consulting network 402 sends, via the at least one communication channel, input from the remote consultant device 434 to the operating room 424 to enable the consultant to interact with a surgical team in the operating room 424 or control the medical equipment 430 in the operating room 424.

In some embodiments, the surgical consulting network 402 notifies, via the at least one computer device in the operating room 424, the surgical team of the received input. In some embodiments, the surgical consulting network 402 sends a request from the operating room 424 for additional input. The surgical consulting network 402 notifies, via the remote consultant device, the surgical consultant of the received request. In some embodiments, the surgical consulting network displays, via the remote consultant device, the patient data associated with the received request. In some embodiments, the surgical consulting network 402 sends the input from the remote consultant device 434 is in response to a consultation request from the surgical team. In some embodiments, the input is video. In some embodiments, the surgical consulting network 402 determines that the surgical consultant should participate in the surgical procedure based on at least one of expertise of the surgical team, surgical support for the surgical procedure, or complexity of the equipment 430 in the operating room 424. In some embodiments, identifying the available surgical consultant is performed in response to determining that the surgical consultant should participate in the surgical procedure.

In some embodiments, the input includes control input for controlling robotic surgical equipment, e.g., the robotic surgical system 160. In some embodiments, the remote consultant device 434 displays a graphical user interface (GUI) for controlling the equipment 430 in the operating room. In some embodiments, the patient data includes real-time video viewable on the remote consultant device 434 by the surgical consultant while providing the input. In some embodiments, the surgical consulting network 402 selects additional patient data for the surgical consultant. In some embodiments, the surgical consulting network 402 sends the selected additional patient data to the surgical consultant. In some embodiments, the patient data includes video or images viewable on the remote consultant device 434 by the surgical consultant. In some embodiments, the surgical consulting network 402 establishes, via the remote consultant device 434, control of at least one surgical apparatus (e.g., medical equipment 430) within the operation room 424 during the surgical procedure. In some embodiments, the surgical consulting network 402 retrieves compensation information of the surgical consultant from the schedule database 408.

In some embodiments, the surgical consulting network 402 determines a payment for the surgical consultant based on the compensation information and the surgical procedure. In some embodiments, the surgical consulting network 402 adjusts a payment balance of the surgical consultant in the consultant database 406. In some embodiments, identifying the available surgical consultant includes determining that information describing the surgical consultant in the consultant database 406 matches a surgical consulting requirement of the medical facility for the surgical procedure. The surgical consulting requirement includes at least one of insurance information of the patient or compensation information of the surgical consultant.

FIG. 5 is a table 500 illustrating an example consultant database 406, in accordance with one or more embodiments. The consultant database 406 is illustrated and described in more detail with reference to FIG. 4. The consultant database 406 can store profile information about physicians and medical technicians who have signed up with the surgical consulting network 402 to be consultants. The surgical consulting network 402 is illustrated and described in more detail with reference to FIG. 4. Likewise, embodiments can include different and/or additional components, or the components can be connected in different orders. Information related to each surgical consultant, such as contact information, consultant user device 434 identification, specialty, availability, surgical consulting rates, account information, etc., are input through the profile module 410. The consultant user device 434 and the profile module 410 are illustrated and described in more detail with reference to FIG. 4.

In some embodiments, a surgical consultant is identified from the consultant database 406 based on a surgical consulting requirement. For example, the consultant data in the consultant database 406 can be accessed by the surgery module 414 to identify surgical consultants that can be brought in to consult on a surgical procedure. The surgery module 414 is illustrated and described in more detail with reference to FIG. 4. A payment module 418 can use the surgical consulting rates and account information to compensate consultants. The payment module 418 is illustrated and described in more detail with reference to FIG. 4. The consultant database 406 can also contain surgical consulting and compensation history data related to each surgical consultant. In one embodiment, a surgical consultant's history and scheduled availability may be stored as a data file.

FIG. 6 is a table 600 illustrating an example schedule database 408, in accordance with one or more embodiments. The schedule database 408 is illustrated and described in more detail with reference to FIG. 4. The schedule database 408 can have one table for each hospital 422, surgical center, or other medical facilities that utilize surgical consultants through the surgical consulting network 402. The hospital 422 and the surgical consulting network 402 are illustrated and described in more detail with reference to FIG. 4. Each facility's table can include scheduled surgeries, connection capabilities, compensation rates, etc. The schedule database 408 can also store the consultants needed and assigned to a given surgery and surgery status and the consultant compensation. Likewise, embodiments can include different and/or additional components, or the components can be connected in different orders.

Figure 7:
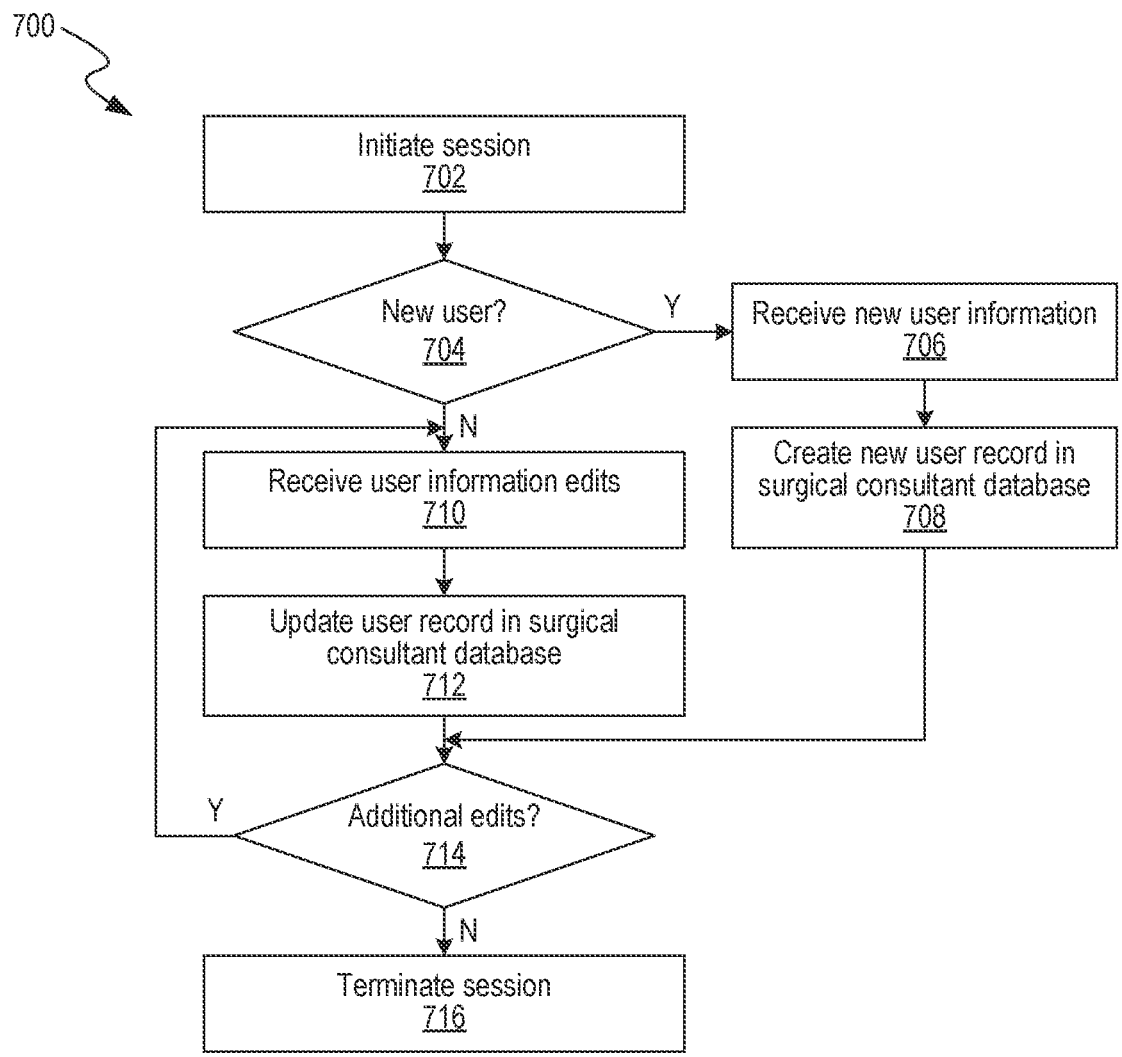
FIG. 7 is a flow diagram illustrating an example process for telepresence-based surgical consulting, in accordance with one or more embodiments.

FIG. 7 is a flow diagram illustrating an example process 700 for telepresence-based surgical consulting, in accordance with one or more embodiments. In some embodiments, the process 700 is performed by the profile module 410 illustrated and described in more detail with reference to FIG. 4. In other embodiments, the process 700 of FIG. 7 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 702, the profile module 410 initiates a session when it receives a message that a surgical consultant has logged in. The message is a text message, an audible alert, a digital signal, an image displayed on a screen, etc., that the profile module 410 can receive and act upon. In step 404, the profile module 410 determines whether the connected surgical consultant is a new or an existing user. In some embodiments, a new profile of a new surgical consultant is generated based on information received describing medical experience of the new surgical consultant. The new profile is stored in the consultant database 406. For example, in step 706, if the user is new, the profile module 410 receives profile data related to the user. The profile data can include information related to the surgical consultant's medical field, medical specialty, the medical equipment 430, the surgical consultant's availability, desired compensation rates, etc. The medical equipment 430 is illustrated and described in more detail with reference to FIG. 4. Information related to financial settlements, such as bank account information, can also be included. In some embodiments, financial settlements are handled by a third-party financial services provider.

In step 708, the profile module 410 generates a profile storing the received data in the consultant database 406. The consultant database 406 is illustrated and described in more detail with reference to FIG. 4. In step 710, if the surgical consultant has an existing profile, additional information or edits to their existing information are received by the profile module 410. In step 712, the profile module 410 updates the surgical consultant's profile in the consultant database 406. In some embodiments, a surgeon having extensive experience in using a piece of medical equipment 430, such as a robotic surgical tool model, can input a schedule of hours they will be available to monitor or assist other surgeons performing surgical procedures using that tool. In step 714, the profile module 410 determines whether the surgical consultant indicates additional edits to be made to their profile. If additional edits are indicated, the profile module 410 returns to step 710. In step 716, if no more edits are indicated, the profile module 410 terminates the session.

Figure 8:
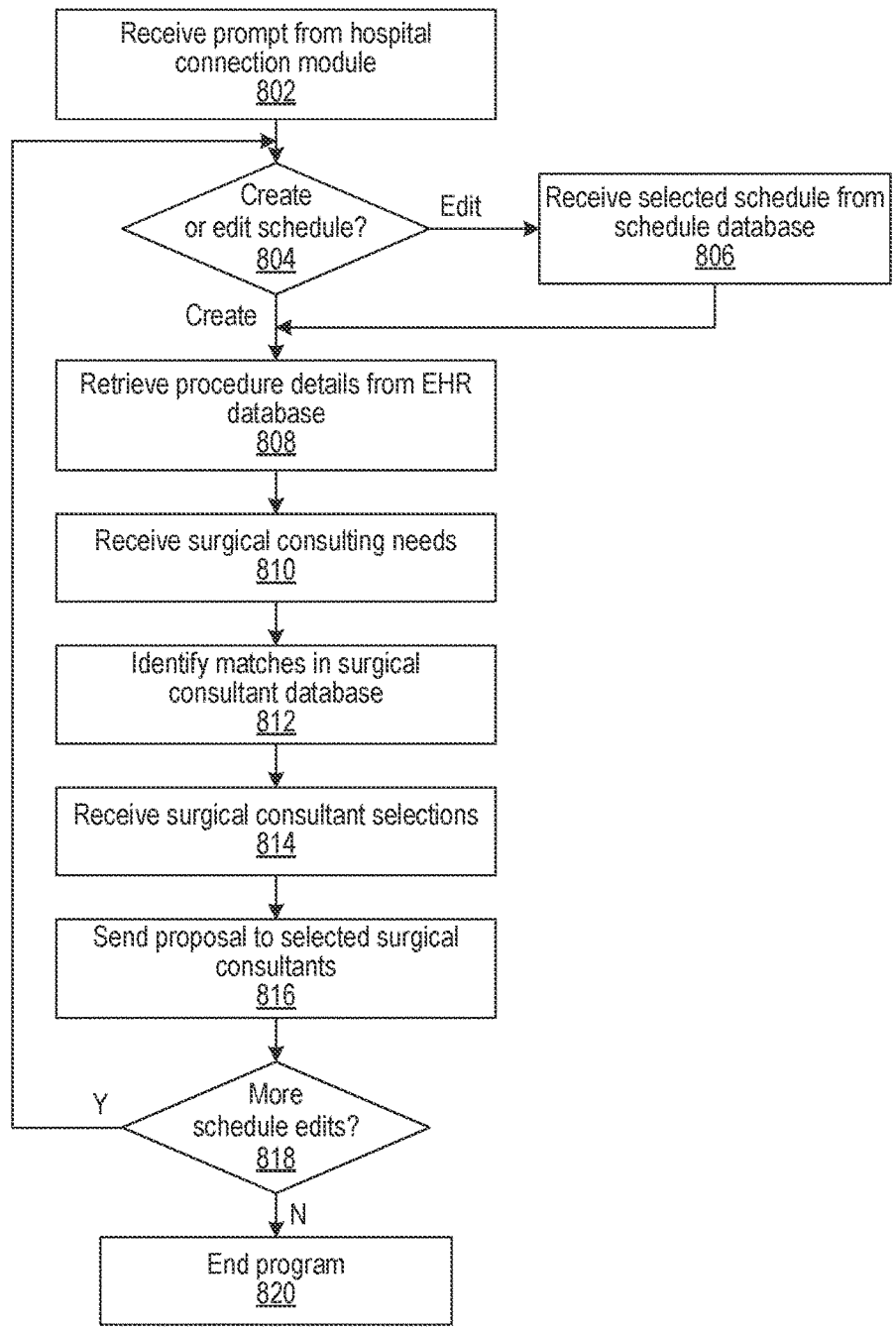
FIG. 8 is a flow diagram illustrating an example process for telepresence-based surgical consulting, in accordance with one or more embodiments.

FIG. 8 is a flow diagram illustrating an example process 800 for telepresence-based surgical consulting, in accordance with one or more embodiments. In some embodiments, the process 800 is performed by the scheduling module 412 illustrated and described in more detail with reference to FIG. 4. In other embodiments, the process 800 of FIG. 8 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In some embodiments, in response to receiving a prompt indicating a surgical procedure from a computer device at a medical facility, the scheduling module 412 schedules the surgical procedure based on patient data retrieved from the EHR 404 database. For example, in step 802, the scheduling module 412 receives a prompt from the hospital connection module 432. The prompt is a message, such as a text message, audible alert, digital signal, image displayed on a screen, etc., that the scheduling module 412 can receive and act upon. The hospital connection module 432 is illustrated and described in more detail with reference to FIG. 4. In step 804, the scheduling module 412 determines whether a new surgical procedure is to be scheduled or whether a surgical procedure that is already scheduled is to be edited. If a new surgical procedure is to be scheduled, the scheduling module 412 proceeds to step 808.

In step 806, if an existing surgical procedure is to be edited, the scheduling module 412 retrieves the indicated surgical procedure from the schedule database 408. The schedule database 408 is illustrated and described in more detail with reference to FIG. 4. In step 808, the scheduling module 412 retrieves the electronic health records for the patient and the surgical procedure indicated from the EHR database 404. The EHR database 404 is illustrated and described in more detail with reference to FIG. 4.

In some embodiments, a surgical consulting requirement of a medical facility for a surgical procedure is received from a computer device at the medical facility. For example, in step 810, the scheduling module 412 receives the surgical consulting requirement of the hospital 422. The hospital 422 is illustrated and described in more detail with reference to FIG. 4. Say a patient is undergoing a partial knee replacement surgery using the medical equipment 430. The medical equipment 430 is illustrated and described in more detail with reference to FIG. 4. For example, the medical equipment 430 are robotic surgical tools, e.g., part of the robotic surgical system 160. The surgical consulting requirement can describe the medical equipment 430 located in the medical facility for performing the surgical procedure. For example, the surgeon performing the procedure wants to have another surgeon who has more experience using the medical equipment 430 in the present surgical procedure available to answer questions during the surgical procedure. The hospital 422 administration wants to have a technician from the maker of the medical equipment 430 available on-call to ensure each device is functioning correctly during the medical equipment 430's use in the hospital 422. In the above example, the surgical consulting requirement of the hospital 422 is received by the scheduling module 412 in step 810.

In some embodiments, a surgical consultant is identified from the consultant database 406 based on a surgical consulting requirement. For example, in step 812, the scheduling module 412 identifies those surgical consultants whose records in the consultant database 406 match some of the criteria received at step 810. The consultant database 406 is illustrated and described in more detail with reference to FIG. 4. In step 814, the scheduling module 412 receives an indication of selecting one or more of the identified surgical consultants. The surgical consultant selection can include specific proposal details, such as the time of a surgical procedure, duties, and compensation terms of the proposed surgical consulting engagement. In some embodiments, engagement information is sent to the consultant user device 434 notifying a surgical consultant of a surgical procedure, in response to identifying the surgical consultant. For example, in step 816, the scheduling module 412 sends the proposal to the selected surgical consultant(s). In step 818, the scheduling module 412 determines whether more schedule edits are indicated. If more schedule edits are indicated, the scheduling module 412 returns to step 804. In step 820, if no further schedule edits are indicated, the scheduling module 412 terminates the session.

Figure 9:
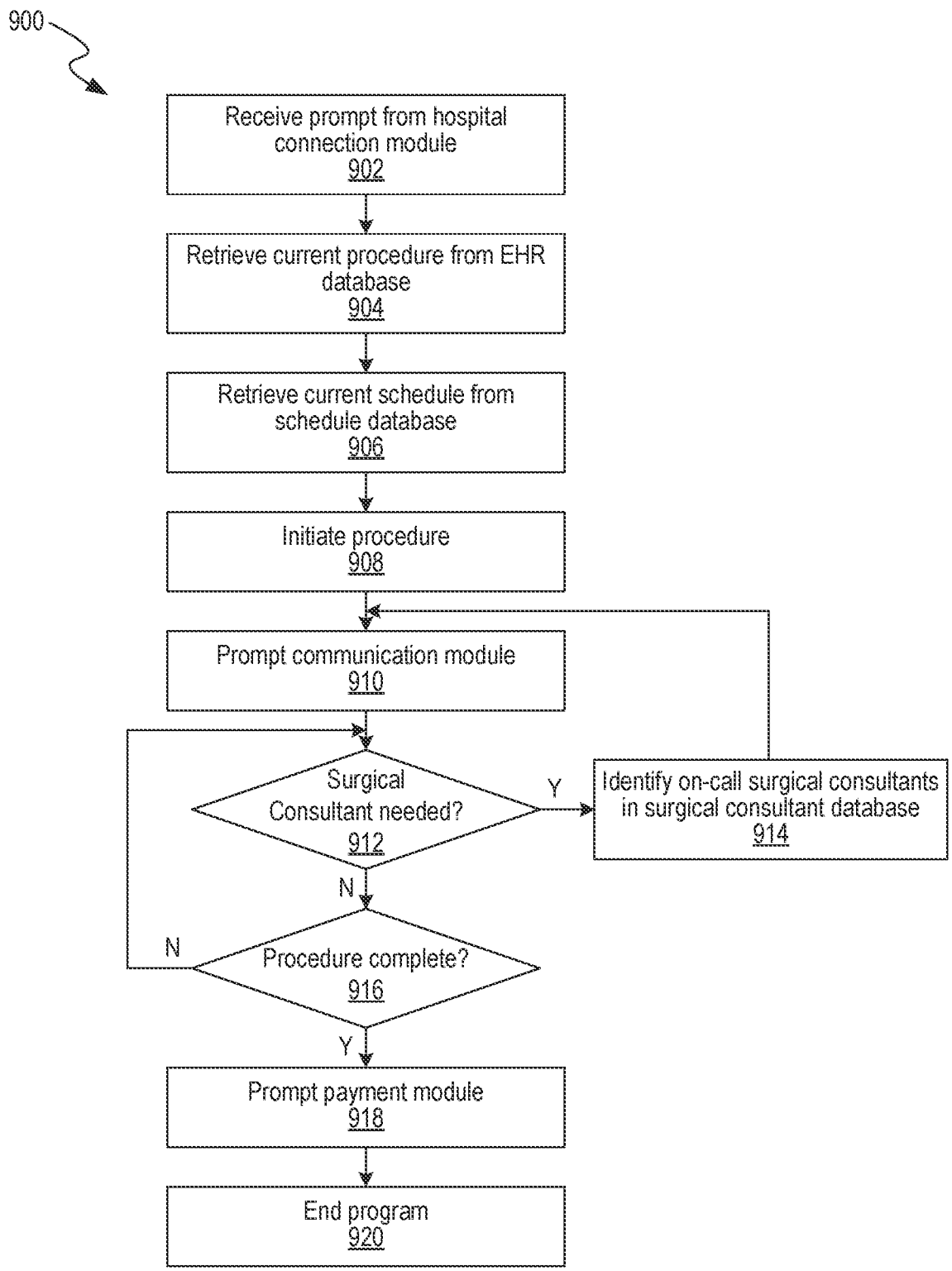
FIG. 9 is a flow diagram illustrating an example process for telepresence-based surgical consulting, in accordance with one or more embodiments.

FIG. 9 is a flow diagram illustrating an example process 900 for telepresence-based surgical consulting, in accordance with one or more embodiments. In some embodiments, the process 900 is performed by the surgery module 414 illustrated and described in more detail with reference to FIG. 4. In other embodiments, the process 900 of FIG. 9 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 902, the surgery module 414 initiates a session when it receives a prompt from the hospital connection module 432. The prompt is a message, such as a text message, audible alert, digital signal, image displayed on a screen, etc., that the surgery module 414 can receive and act upon. The hospital connection module 432 is illustrated and described in more detail with reference to FIG. 4. In step 904, the surgery module 414 retrieves the patient's electronic health records related to the present surgical procedure from the EHR database 404. The EHR database 404 is illustrated and described in more detail with reference to FIG. 4. In step 906, the surgery module 414 retrieves the surgical schedule related to the present surgical procedure from the schedule database 108. The schedule database 108 is illustrated and described in more detail with reference to FIG. 4. A medical professional can then initiate the surgical procedure in the operating room 424. The operating room 424 is illustrated and described in more detail with reference to FIG. 4. In some embodiments, a message is received that the surgical procedure has been initiated. For example, a surgeon performing the surgical procedure indicates (the message) to the digital assistant interface 428 that they are ready to begin, using a verbal cue. The digital assistant interface 428 is illustrated and described in more detail with reference to FIG. 4. In other embodiments, a robotic surgical system 160 initiates the surgical procedure in the operating room 424. The robotic surgical system 160 is illustrated and described in more detail with reference to FIG. 1.

In step 910, the surgery module 414 prompts and initiates the communication module 416. The communication module 416 is illustrated and described in more detail with reference to FIG. 4. The prompt is a message, such as a text message, audible alert, digital signal, image displayed on a screen, etc., that the communication module 416 can receive and act upon. The communication module 416 connects the surgical consultant(s) to the operating room 424. In step 912, the surgery module 414 determines whether there is an indication of a need for additional surgical consultants for the present surgical procedure. If no additional surgical consultants are indicated, the surgery module 414 proceeds to step 916. In step 914, if a need for one or more additional surgical consultants is indicated, certain on-call consultants in the consultant database 406 who meet the criteria indicated at step 912 are identified. The consultant database 406 is illustrated and described in more detail with reference to FIG. 4. Engagement with one or more of the identified on-call surgical consultants causes the surgery module 414 to return to step 910. In step 912, if no further indications of additional surgical consulting are received, the surgery module 414 proceeds to step 916 and determines whether the surgical procedure is complete. In some embodiments, it is determined that a surgical procedure has been completed. In response to determining that the surgical procedure has been completed, the communication channel is terminated.

If the surgical procedure is not complete, the surgery module 414 returns to step 912. In step 918, if the procedure is complete, the surgery module 414 prompts the payment module 418. The payment module 418 is illustrated and described in more detail with reference to FIG. 4. The prompt is a message, such as a text message, audible alert, digital signal, image displayed on a screen, etc., that the payment module 418 can receive and act upon. In step 920, upon receipt of the notification that the payment module 418 has completed its processing, the surgery module 414 terminates the session.

Figure 10:
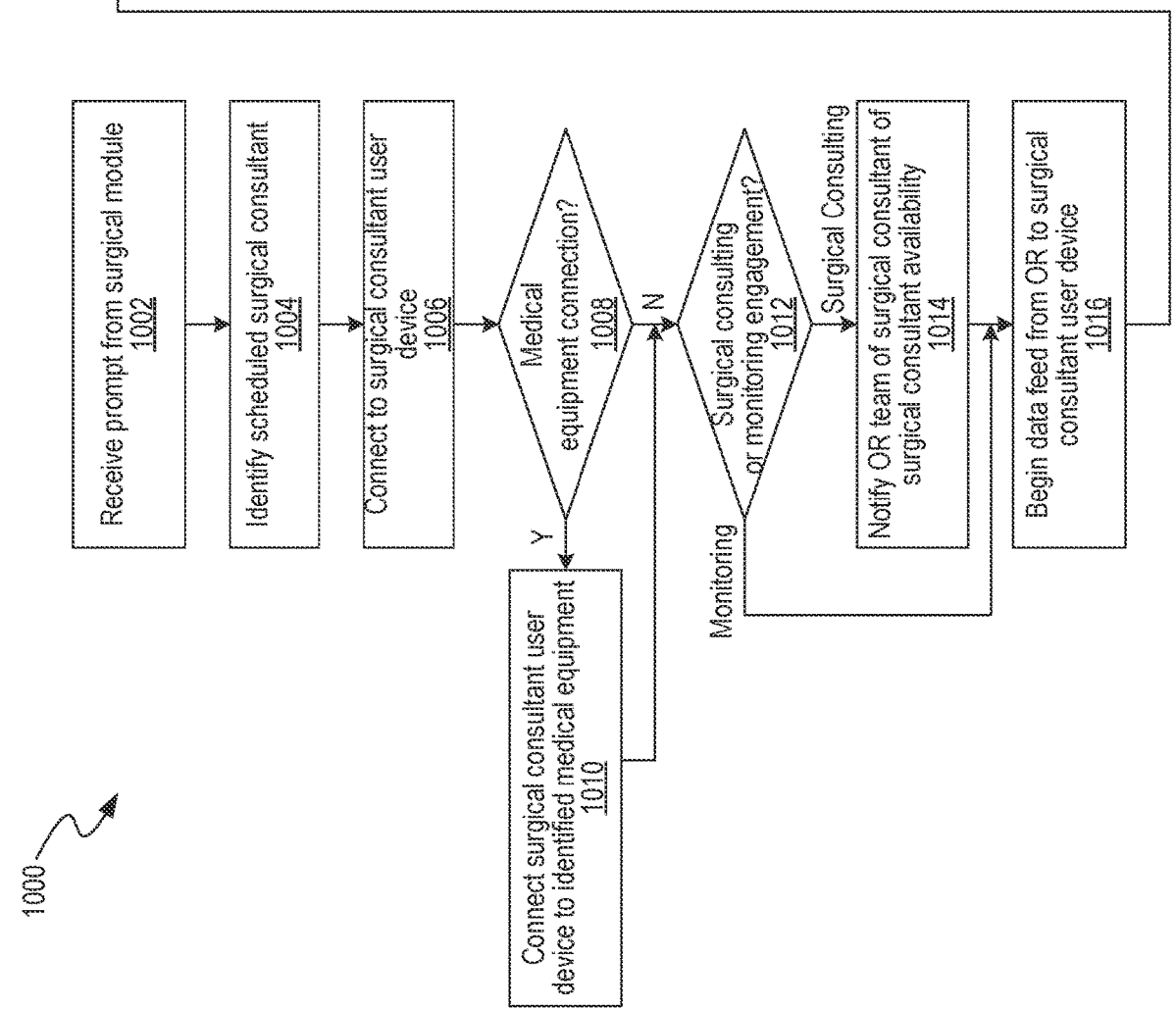
FIG. 10 is a flow diagram illustrating an example process for telepresence-based surgical consulting, in accordance with one or more embodiments.

FIG. 10 is a flow diagram illustrating an example process 1000 for telepresence-based surgical consulting, in accordance with one or more embodiments. In some embodiments, the process 1000 is performed by the communication module 416 illustrated and described in more detail with reference to FIG. 4. In other embodiments, the process 1000 of FIG. 10 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the communication module 416 initiates a session when it receives a prompt from the surgery module 114. The prompt is a message, such as a text message, audible alert, digital signal, image displayed on a screen, etc., that the communication module 416 can receive and act upon. The surgery module 414 is illustrated and described in more detail with reference to FIG. 4. The schedule database 408 indicates one or more surgical consultants scheduled to be engaged in the present surgical procedure. The schedule database 408 is illustrated and described in more detail with reference to FIG. 4. In step 1004, the communication module 416 identifies the records of the one or more surgical consultants from the consultant database 406. The consultant database 406 is illustrated and described in more detail with reference to FIG. 4.

In some embodiments, a surgical consultant engaged is a technician from the medical equipment maker of a piece of medical equipment 430, such as a robotic surgical tool. The medical equipment 430 is illustrated and described in more detail with reference to FIG. 4. In some embodiments, it is determined that a connection between the consultant user device 434 and the medical equipment 430 at a medical facility is required for the surgical procedure based on engagement information. The connection is implemented using the network adapter 312 and the network 314. A data feed is initiated on a sensor 426 and the medical equipment 430 at the medical facility, in response to determining that the connection is required. For example, the surgical consultant is engaged to monitor the function of the medical equipment 430 to identify any potential defects and faults in the medical equipment 430 or its operation prior to or during surgery. In some embodiments, the surgical consultants engaged are a group of medical students observing a surgical procedure as part of a class. In some embodiments, the surgical consultant engaged is an anesthesiologist who monitors a patient and controls an anesthesiology machine 140 based on data received from one or more sensors 426. The anesthesiology machine 140 is illustrated and described in more detail with reference to FIG. 1. The sensors 426 are illustrated and described in more detail with reference to FIG. 4. In some embodiments, a surgical consultant engaged is a surgeon with experience with the present type of surgical procedure.

In some embodiments, a communication channel is established between a computer device at a medical facility and the consultant user device 434 of a surgical consultant. The communication channel is for the surgical consultant to provide surgical consulting related to a surgical procedure. The communication is a link over which text, audio, or video is transmitted. The communication channel is implemented using the network 314 and the network adapter 312 illustrated and described in more detail with reference to FIG. 3. For example, in step 1106, the communication module 416 connects to the consultant user device 434. The consultant user device 434 is illustrated and described in more detail with reference to FIG. 4.

In step 1108, the communication module 416 determines whether a connection to the medical equipment 430 is needed as part of the surgical consultant's engagement. For example, medical students observing the surgical procedure would not need a connection to the anesthesiology machine 140. In another example, an anesthesiologist needs to connect to an anesthesiology machine 140 in the operating room 424. The operating room 424 is illustrated and described in more detail with reference to FIG. 4. If no such connection is indicated, the communication module 416 proceeds to step 1012. In step 1010, if a connection is indicated, the consultant user device 434 is connected to the identified equipment.

In step 1012, the communication module 416 determines whether the present surgical consulting engagement is a surgical consulting or monitoring engagement. For example, medical students may be monitoring a procedure as part of a medical school class. In another example, a surgeon with experience in the present surgical procedure may be consulting with the surgeon performing the surgical procedure. In step 1012, if a monitoring engagement is identified, the communication module 416 proceeds to step 1016. In step 1014, if the engagement is for surgical consulting, the communication module 416 notifies the team of practitioners, such as the surgeon(s), anesthesiologist(s), or nurse(s) in the operating room 424. The communication module 416 can notify the team of practitioners using the digital assistant interface 428 that the engaged surgical consultant is connected to the surgical consulting network 402. The digital assistant interface 428 and the surgical consulting network 402 are illustrated and described in more detail with reference to FIG. 4.

In step 1016, the communication module 416 initiates a data feed on the sensors 426 and the medical equipment 430 indicated in the schedule database 408. In step 1018, the communication module 416 determines whether there is an indication of input from the surgical consulting module 120 of a surgical consultant. If there is no input from the surgical consulting module 120 of the surgical consultant, the communication module 416 proceeds to step 1022. If surgical consultant input is indicated at step 1018, the communication module 416 sends a notification to the operating room 424 using the digital assistant interface 428. In one example, a surgical consulting surgeon identifies an issue in an operating surgeon's technique and delivers verbal instructions to the operating surgeon. In some embodiments, input is received from the consultant user device 434. The input is related to a surgical procedure. In response to receiving the input, a notification of the input is sent to the digital assistant interface 428 at a medical facility over a communication channel. In some embodiments, information is sent describing an adjustment to the medical equipment 430 at the medical facility, in response to receiving the input. For example, an anesthesiologist adjusts the medical equipment 430, and a change in settings is displayed by the digital assistant interface 428.

In step 1022, the communication module 416 determines whether a need for one or more additional surgical consultants is indicated. If no indication of an additional surgical consultant's need is determined at step 1022, the communication module 416 determines in step 1024 whether the surgical procedure is complete. In some embodiments, optical recognition is used by a robotic surgical system 160 to identify the movement and positions of various people or things in the operating room 424 that indicate a complete surgical procedure. The robotic surgical system 160 is illustrated and described in more detail with reference to FIG. 1. In step 1024, if no indication that the surgical procedure is complete is received, the communication module 416 proceeds to step 1018. In step 1024, if an indication of either the surgical procedure's completion or the need for one or more additional consultants is received, in step 1026, the communication module 416 hands off control to the surgery module 414.

Figure 11:
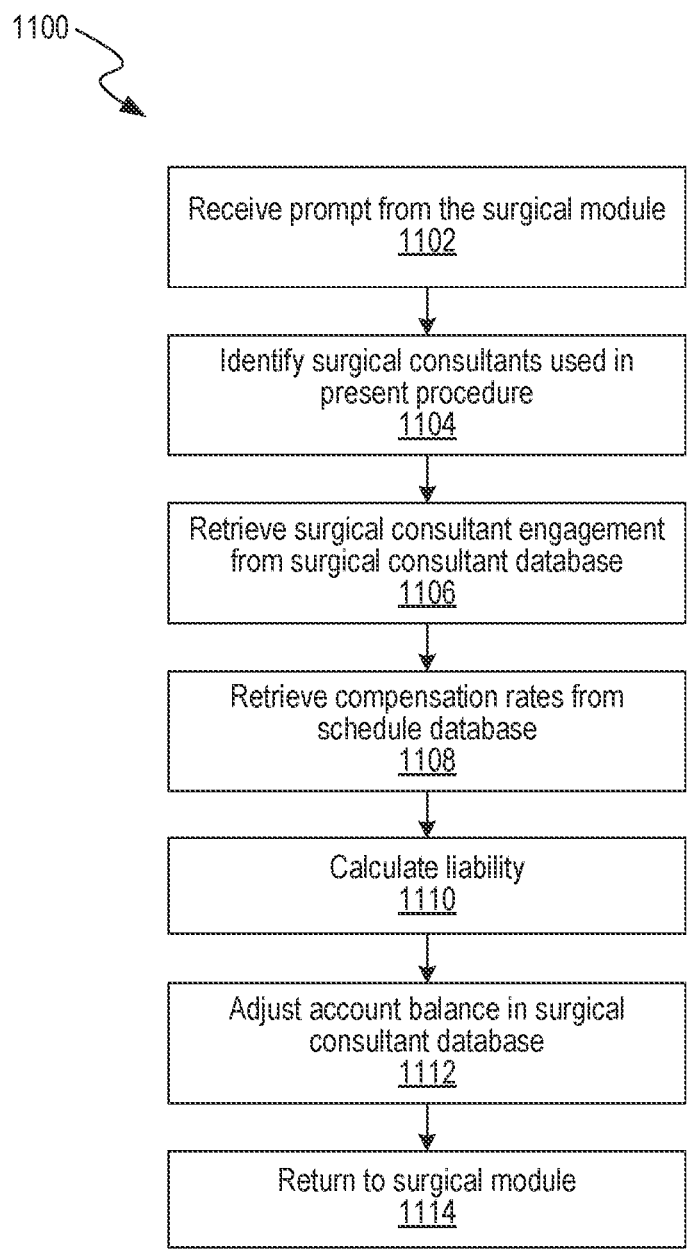
FIG. 11 is a flow diagram illustrating an example process for telepresence-based surgical consulting, in accordance with one or more embodiments.

FIG. 11 is a flow diagram illustrating an example process 1100 for telepresence-based surgical consulting, in accordance with one or more embodiments. In some embodiments, the process 1100 is performed by the payment module 418 illustrated and described in more detail with reference to FIG. 4. In other embodiments, the process 1100 of FIG. 11 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1102, the payment module 418 initiates a session when it receives a prompt from the surgery module 414, indicating that the present surgical procedure is complete. The prompt is a message, such as a text message, audible alert, digital signal, image displayed on a screen, etc., that the payment module 418 can receive and act upon. The surgery module 414 is illustrated and described in more detail with reference to FIG. 4. In step 1104, the payment module 418 identifies the consultant(s) engaged in the present surgical procedure. In step 1106, the payment module 418 retrieves the details of each identified surgical consultant's consulting engagement from the consultant database 406. The consultant database 406 is illustrated and described in more detail with reference to FIG. 4.

In step 1108, the payment module 418 retrieves the surgical consulting engagement's compensation rate(s) from the schedule database 408. The schedule database 408 is illustrated and described in more detail with reference to FIG. 4. In step 1110, the payment module 418 determines the liability of one or more parties. For example, a surgeon is engaged to provide medical guidance as needed to an operating surgeon performing the present surgical procedure. The surgical consultant is observed by the communication module 416 to have been engaged for the operating surgeon's guidance three times. The communication module 416 is illustrated and described in more detail with reference to FIG. 4. In the example, the surgical consulting engagement terms indicate the surgical consultant is to be paid $5,000 for being available on-call for the surgical procedure and an additional $1,000 for each instance of medical guidance provided. The hospital 422's total liability to the surgical consulting surgeon would be $8,000. The hospital 422 is illustrated and described in more detail with reference to FIG. 4.

In another example, an anesthesiologist is engaged at a flat rate of $10,000 to control one or more pieces of the medical equipment 430 during the present surgical procedure. In another example, the engaged surgical consultants are medical students observing the surgical procedure for a medical school class. In the example, the hospital 422 is a teaching hospital. The present surgical consulting engagement indicates that the hospital 422 should receive payment from the medical students or from the educational institution they are associated with, for each instance of the surgeon answering the students' questions during the procedure. In step 1112, the payment module 418 makes the corresponding adjustments to balances in the consultant database 406. In step 1114, the payment module 418 returns control to the surgery module 114.

Figure 12:
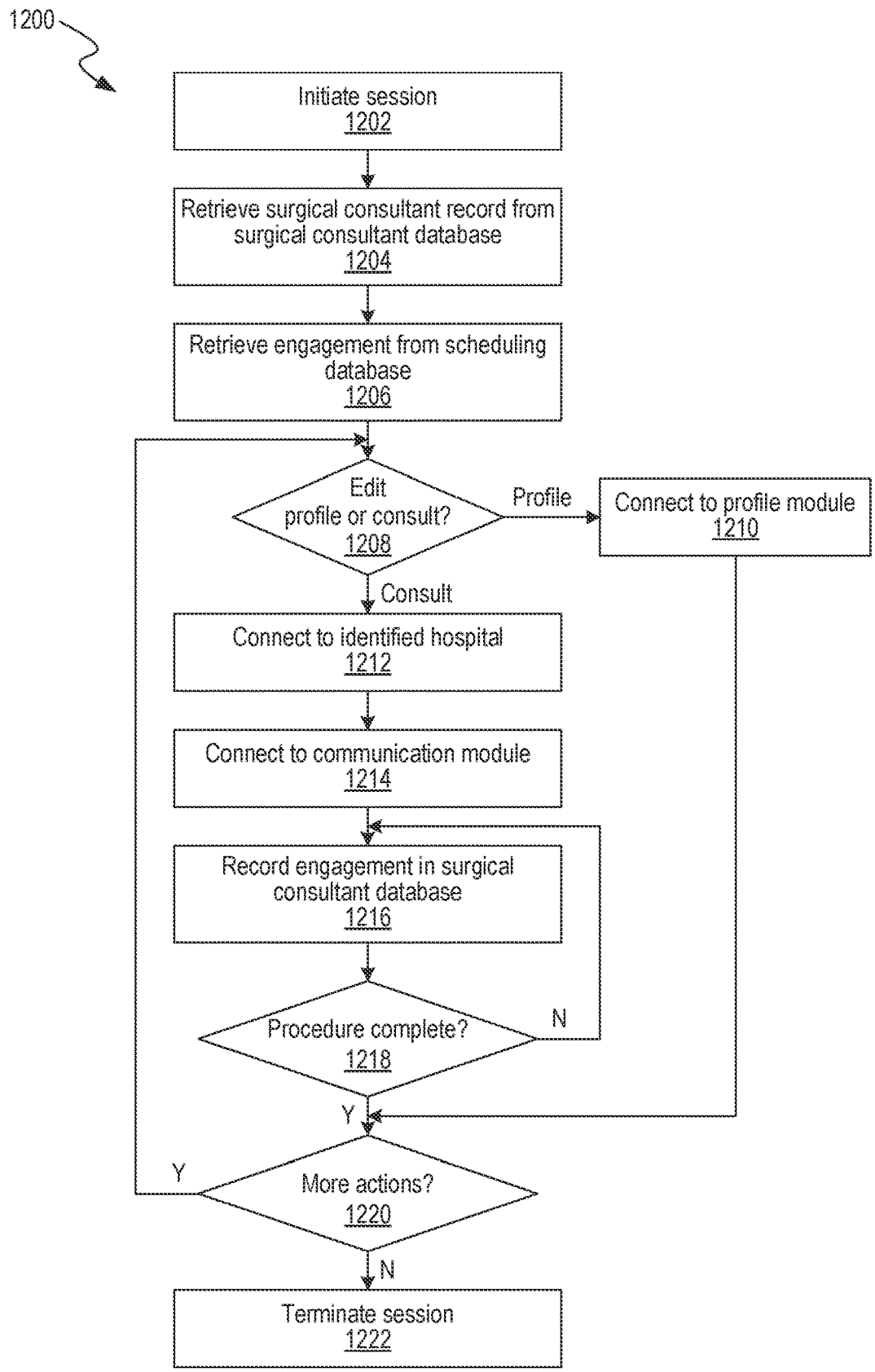
FIG. 12 is a flow diagram illustrating an example process for telepresence-based surgical consulting, in accordance with one or more embodiments.

FIG. 12 is a flow diagram illustrating an example process 1200 for telepresence-based surgical consulting, in accordance with one or more embodiments. In some embodiments, the process 1200 is performed by the surgical consulting module 420 illustrated and described in more detail with reference to FIG. 4. In other embodiments, the process 1200 of FIG. 12 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1202, the surgical consulting module 420 initiates a session when a user logs in. In step 1204, the surgical consulting module 420 retrieves the account record for the present user from the consultant database 406. The consultant database 406 is illustrated and described in more detail with reference to FIG. 4. In step 1206, the surgical consulting module 420 retrieves engagements indicated in the retrieved account record from the schedule database 408.

The schedule database 408 is illustrated and described in more detail with reference to FIG. 4. In step 1208, the surgical consulting module 420 can receive an indication of (1) an edit to the user's account record in the consultant database 406 or (2) a surgical consulting engagement being initiated. In step 1208, if a profile edit is indicated, the profile module 410 is initiated. The profile module 410 is illustrated and described in more detail with reference to FIG. 4. In step 1212, if a surgical consulting engagement is indicated, the consultant user device 434 is connected to the identified hospital 422. The consultant user device 434 and the hospital 422 are illustrated and described in more detail with reference to FIG. 4.

In step 1214, the surgical consulting module 420 connects the consultant user device 434 to the communication module 416. The communication module 416 is illustrated and described in more detail with reference to FIG. 4. In step 1216, the engagement of the surgical consultant is recorded in the consultant database 406. For example, medical students' answers to computer or teacher-generated questions are recorded. In another example, the number of adjustments to medical equipment 430 made by a surgical consulting anesthesiologist is recorded. The medical equipment 430 is illustrated and described in more detail with reference to FIG. 4. In step 1218, the surgical consulting module 420 determines whether the surgical procedure is complete. If the surgical procedure is not complete, the surgical consulting module 420 returns to step 1216. In step 1220, if the surgical consulting module 420 determines that the surgical procedure is complete or if the profile module 110 has completed, the surgical consulting module 420 determines whether more actions are indicated by the surgical consultant. If more actions are indicated at step 1220, the surgical consulting module 420 returns to step 1208. In step 1220, if the surgical consulting module 420 determines that more actions are not indicated, the surgical consulting module 420 terminates the session at step 1222.

Figure 13:
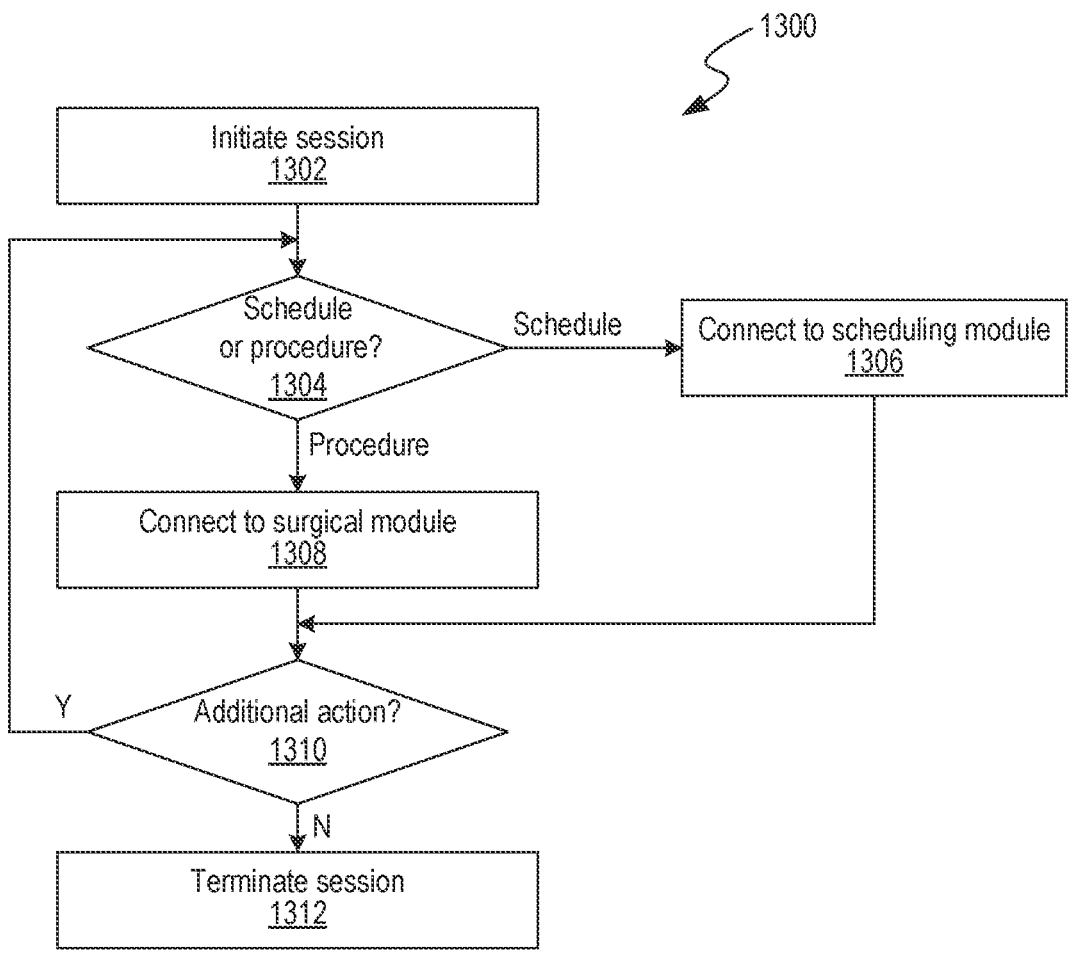
FIG. 13 is a flow diagram illustrating an example process for telepresence-based surgical consulting, in accordance with one or more embodiments.

FIG. 13 is a flow diagram illustrating an example process 1300 for telepresence-based surgical consulting, in accordance with one or more embodiments. In some embodiments, the process 1300 is performed by the hospital connection module 432 illustrated and described in more detail with reference to FIG. 4. In other embodiments, the process 1300 of FIG. 13 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1302, the hospital connection module 432 initiates a session when a user associated with the hospital 422 logs in to the system 402. The hospital 422 and the system 402 are illustrated and described in more detail with reference to FIG. 4. In step 1304, the hospital connection module 432 can receive an indication of a schedule adjustment or procedure to initiate. In step 1304, if a schedule adjustment is indicated, the hospital connection module 432 prompts the scheduling module 412 to initiate at step 1306. The scheduling module 412 is illustrated and described in more detail with reference to FIG. 4. In step 1304, if a procedure initiation is indicated, the hospital connection module 432 connects to and initiates the surgery module 406 in step 1308. The surgery module 406 is illustrated and described in more detail with reference to FIG. 4. In step 1310, the hospital connection module 432 determines whether the user indicates additional actions. In step 1310, if additional actions are indicated, the hospital connection module 432 returns to step 1304. If no additional actions are indicated in step 1310, the hospital connection module 432 terminates the session at step 1312.

Figure 14A:
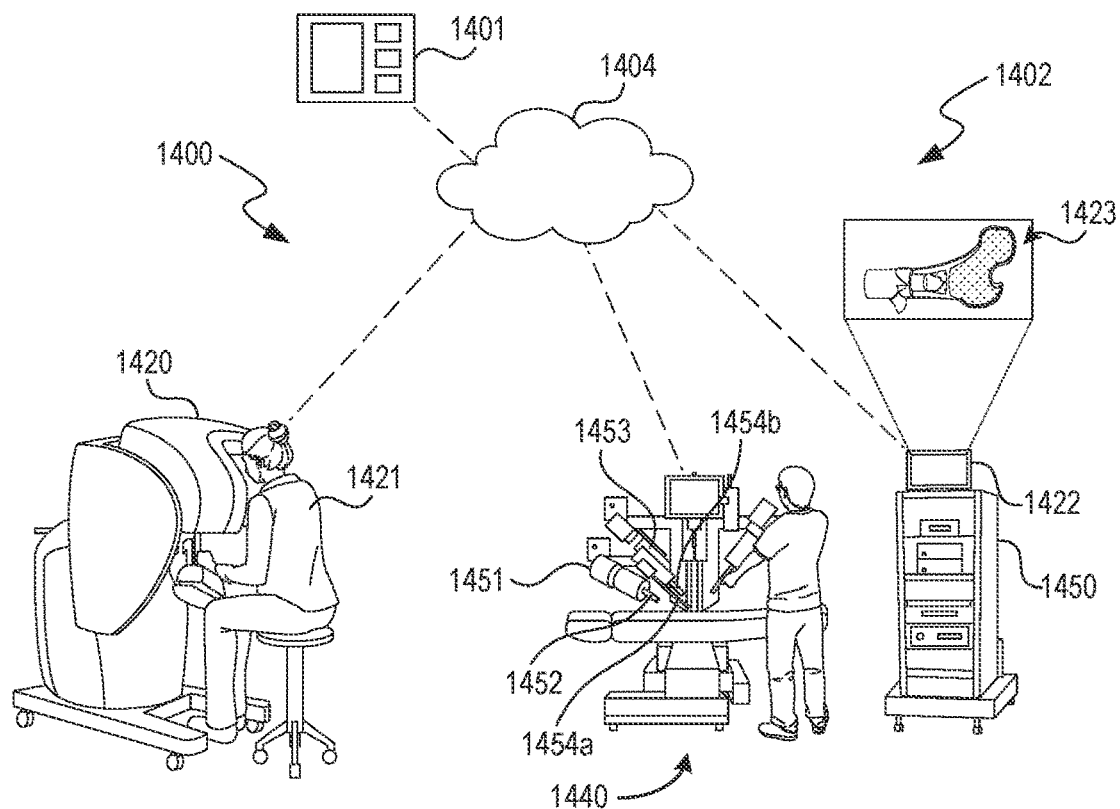
FIG. 14A is a block diagram illustrating an example robotic surgical system, in accordance with one or more embodiments.

FIG. 14A is a block diagram illustrating an example robotic surgical suite or system 1400 ("robotic surgical system 1400"), in accordance with one or more embodiments. The robotic surgical system 1400 is the same as or similar to the robotic surgical system 160 illustrated and described in more detail with reference to FIG. 1. The robotic surgical system 1400 can include components and features discussed in connection with FIGS. 1-3 and 14B-15. For example, the robotic surgical system 1400 can include a console 1420 with features of the console 108 of FIG. 1. Likewise, the components and features of FIG. 14A can be included or used with other embodiments disclosed herein. For example, the description of the input devices of FIG. 14A applies equally to other input devices (e.g., input devices 166 of FIG. 1). The robotic surgical system 1400 can be configured to provide telepresence control by one or more consultants at remote locations based on a pre-operative surgical plan, inter-operative surgical event(s) at the surgical suite, etc. Machine learning algorithms and other techniques disclosed herein can be used to manage surgical suite resources, schedule consultants, manage permission rights, and/or adjust network flow to improve surgical outcomes. For example, flow of network traffic at the surgical suite can be controlled to maintain a threshold level of control of the medical equipment by the user.

The robotic surgical system 1400 includes a user device or console 1420 ("console 1420"), a surgical robot 1440, and a computer, controller, or data system 1450. The console 1420 can be on-site or at a remote location and operated by a surgeon and can communicate with components in a surgical suite or an operating room 1402 ("operating room 1402"), remote devices/servers, a network 1404, or databases (e.g., database 106 of FIG. 1) via the network 1404. The robotic surgical system 1400 can include surgical control software and can include a guidance system (e.g., ML guidance system, AI guidance system, etc.), surgical planning software, event detection software, surgical tool software, etc., or other features disclosed herein to perform surgical step(s) or procedures or implement steps of processes discussed herein.

A consultant device 1401 can communicate via the network 1404 with components of the robotic surgical system 1400, monitoring equipment, or other components of the robotic surgical system 1400. The surgical robot 1440, or other components disclosed herein, can communicate with and send collected data (e.g., sensor readings, instrument data, surgical robot data, etc.) to at least one database or data system 1450, which are accessible to the consultant(s). This information can be used to, for example, create new machine-learning training data sets, generate procedure plans, perform future simulations, post-operatively analyze surgical procedures, or the like. The controller or data system 1450 can be incorporated, used with, or otherwise interact with other databases, systems, and components disclosed herein. In some embodiments, the data system 1450 can be incorporated into the surgical robot 1440 or other systems disclosed herein. In some embodiments, the data system 1450 can be located at a remote location and can communicate with a surgical robot via one or more networks. For example, the data system 1450 can communicate with a hospital via a network, such as a wide area network, a cellular network, etc. One or more local networks at the hospital can establish communication channels between pieces of surgical equipment within the surgical room. A mobile network test module may measure the latency of the wireless communication established between the robotic surgical system and the consultant device 1401 to manage network flow. A measured/determined latency of a wireless network may be the same as a latency of a network that includes the wireless network, where the network may include a starting point/node for data to be transmitted to an ending point/node, and where the data is communicated by one computer/device associated with a surgical site to another computer/device associated with a location of the remote physician/surgeon. Scheduling of consultants can be based, at least in part, on expected latency (e.g., latency within the network 1404 or other network) required to perform the telesurgery based on the received one or more surgery data. For example, a scheduling module may be configured to determine the requirement of the bandwidth (e.g., 10 MHz, 20 MHz, 30 MHz, etc.) needed and/or expected latency (e.g., ±50 milliseconds, ±70 milliseconds, ±100 milliseconds, etc.). The parameters for scheduling participation of the consultant device 1401 can be selected by a surgical team, healthcare provider, or the like.

The user 1421 can use the console 1420 to view and control the surgical robot 1440. The console 1420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 1420 can include a clutch pedal to allow the user 1421 to disengage one or more sensor-actuator components from control by the surgical robot 1440. The console 1420 can also include display or output so that the one of more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 1400 can include multiple consoles 1420 to allow multiple users to simultaneously or sequentially perform portions of a surgical procedure. The term "simultaneous" herein refers to actions performed at the same time or in the same surgical step. The number and configuration of consoles 1420 can be selected based on the surgical procedure to be performed, number and configurations of surgical robots, surgical team capabilities, or the like.

Figure 14B:
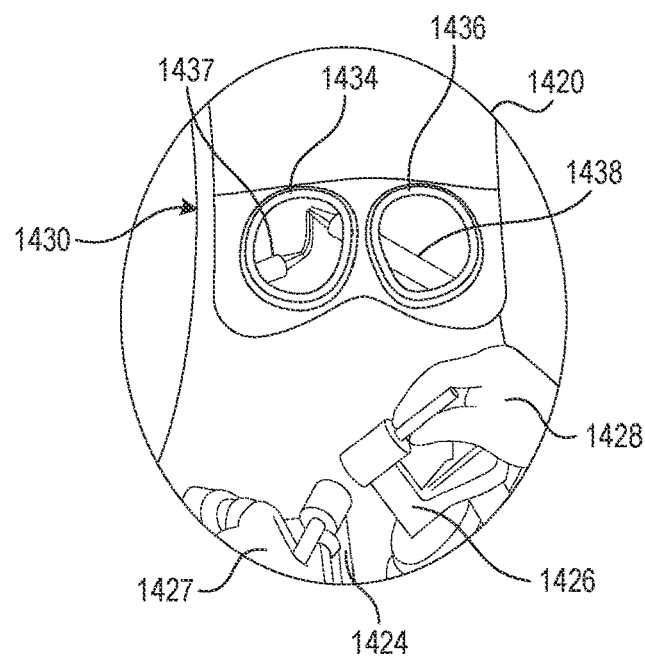
FIG. 14B illustrates an example console of the robotic surgical system of FIG. 14A, in accordance with one or more embodiments.

FIG. 14B illustrates an example console 1420 of the robotic surgical system 1400 of FIG. 14A, in accordance with one or more embodiments. The console 1420 includes hand-operated input devices 1424, 1426, illustrated held by the user's left and right hands 1427, 1428, respectively. A viewer 1430 includes left and right eye displays 1434, 1436. The user can view, for example, the surgical site, instruments 1437, 1438, or the like. The user's movements of the input devices 1424, 1426 can be translated in real-time to, for example, mimic the movement of the user on the viewer 1430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 1420 can be located at the surgical room or at a remote location.

The viewer 1430 can display at least a portion of a surgical plan, including multiwavelength images, image modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 1430 can be a VR/AR headset, display, or the like. The robotic surgical system 1400, illustrated and described in more detail with reference to FIG. 14A, can further include multiple viewers 1430 so that multiple members of a surgical team can view the surgical procedure. The number and configuration of the viewers 1430 can be selected based on the configuration and number of surgical robots.

Referring again to FIG. 14A, the surgical robot 1440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 1440 can be selected based on the procedures to be performed.

The surgical robot 1440 can operate in different modes selected by a user, set by the surgical plan, and/or selected by the robotic surgical system 1400. In some procedures, the surgical robot 1440 can remain in the same mode throughout a surgical procedure. In other procedures, the surgical robot 1440 can be switched between modes any number of times. The configuration, functionality, number of modes, and type of modes can be selected based on the desired functionality and user control of the robotic surgical system 1400. The robotic surgical system 1400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 1421 controls, via the console 1420, movement of the surgical robot 1440. The user's movements of the input devices can be translated in real-time into movement of end effectors 1452 (one identified).

In a semi-autonomous mode, the user 1421 controls selected steps and the surgical robot 1440 autonomously performs other steps. For example, the user 1421 can control one robotic arm to perform one surgical step while the surgical robot 1440 autonomously controls one or more of the other arms to concurrently perform another surgical step. In another example, the user 1421 can perform steps suitable for physician control. After completion, the surgical robot 1440 can perform steps involving coordination between three or more robotic arms, thereby enabling complicated procedures. For example, the surgical robot 1440 can perform steps involving four or five surgical arms, each with one or more end effectors 1452. The surgical robot 1440 can include a multi-modality imager 1453 having imaging devices 1454a, 1454b (collectively "imaging devices 1454"). The imaging devices 1454 can be, for example, PET scanners, ultrasound imagers, MRI imagers, CT scanners, cameras (e.g., camera imager hardware, digital cameras, etc.), infrared imagers, etc. In embodiments, the surgical robot 1440 retrieves/receives images from standalone X-ray machines, MRI machines, CT scanners, etc. Example imaging devices and imaging modalities are discussed in connection with FIGS. 1, 14A, and 16. The number, imaging capabilities, and configurations of the imaging devices 1454 can be selected based on the imaging to be performed.

The robotic surgical system 1400 can automatically generate multi-modality images based on surgical plans and then perform one or more surgical steps of a planned surgical procedure. In embodiments, the robotic surgical system 1400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 1400 can generate the imaging plan based on imaging capabilities of the multi-modality imager 1453. The robotic surgical system 1400 can notify the surgical team to add or replace imaging devices 1454 to achieve the desired imaging capability.

The robotic surgical system 1400 can retrieve available images of a patient from, for example, electronic medical records, image databases, and/or other imaging sources. The robotic surgical system 1400 can identify and retrieve images that can be processed for producing one or more multi-modality images. The robotic surgical system 1400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 1400 retrieves available images and determines imaging programs or parameters (e.g., positions, imaging settings, etc.) of one or more of the imaging devices 1454 corresponding to the available images. In embodiments, a machine learning system (see FIG. 2) can be used to generate imaging plans based on training sets. The training sets can include, for example, single modality training sets, composite multi-modality training sets, confirmed diagnostic training sets, and other training sets. This allows the robotic surgical system 1400 to perform re-training procedures for continuously or periodically training the machine learning system. Newly-captured images can be keyed to or matched with the retrieved images, thereby increasing accuracy of the multi-modality images. During intro-operative imaging, the images can be analyzed in real-time to further control the robotic surgical system 1400.

In an autonomous mode, the surgical robot 1440 can autonomously perform steps under the control of the data system 1450. The robotic surgical system 1400 can be pre-programmed with instructions for performing the steps autonomously. For example, command instructions can be generated based on a surgical plan. The surgical robot 1440 autonomously performs steps or the entire procedure. The user 1421 and surgical team can observe the surgical procedure to modify or stop the procedure. Advantageously, complicated procedures can be autonomously performed without user intervention to enable the surgical team to focus and attend to other tasks. Although the robotic surgical system 1400 can autonomously perform steps, the surgical team can provide information in real-time that is used to continue the surgical procedure. The information can include surgical robot input, surgical team observations, and other data input.

The robotic surgical system 1400 can also adapt to the user control to facilitate completion of the surgical procedure. In some embodiments, the robotic surgical system 1400 can monitor, via one or more sensors, at least a portion of the surgical procedure performed by the surgical robot 1440. The robotic surgical system 1400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 1400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds, as discussed in connection with FIG. 12. The adverse surgical events can be identified using a machine learning model trained using, for example, prior patient data, training sets (e.g., tool data), etc.

In some embodiments, the robotic surgical system 1400 determines whether a detected event (e.g., operational parameters outside a target range or exceeding a threshold, etc.) is potentially an adverse surgical event based on one or more criteria set by the robotic surgical system 1400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 1400 can take other actions in response to identification of an event. If the robotic surgical system 1400 identifies an end effector malfunction or error, the robotic surgical system 1400 can stop usage of the end effector and replace the malfunctioning component (e.g., surgical tool or equipment) to complete the procedure. The robotic surgical system 1400 can monitor hospital inventory, available resources in the surgical room 1402, time to acquire equipment (e.g., time to acquire replacement end effectors, surgical tools, or other equipment), and other information to determine how to proceed with surgery. The robotic surgical system 1400 can generate multiple proposed surgical plans for continuing with the surgical procedure. The user and surgical team can review the proposed surgical plans to select an appropriate surgical plan. The robotic surgical system 1400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 1400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 1400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 1440 can include robotic arms 1451 (one identified) with robotic links, motors, and integrated or removable end effectors 1452 (one identified). The end effectors 1452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 1440 to provide more intelligent and intuitive results.

The data system 1450 can improve surgical planning, monitoring (e.g., via the display 1422), data collection, surgical robotics/navigation systems, intelligence for selecting instruments, implants, etc. The data system 1450 can execute, for example, surgical control instructions or programs for a guidance system (e.g., ML guidance system, AI guidance system, etc.), surgical planning programs, event detection programs, surgical tool programs, etc. For example, the data system 1450 can increase procedure efficiency and reduce surgery duration by providing information insertion paths, surgical steps, or the like. The data system 1450 can be incorporated into or include other components and systems disclosed herein. As shown by FIG. 14A, the display 1422 can display, for example, a diagnosis of tissue, images, maps, surgical plans, etc. For example, the display 1422 can display a diagnostic image or map showing, for example, a bone in image 1423 (discussed in more detail below with reference to multi-modality imaging), regions of interest (e.g., zones of diseased tissue, regions of tissue with specific characteristic(s), margins, etc.), features of interest, anatomical elements (e.g., cartilage, soft tissue, etc.), or the like. An example image is discussed in connection with FIG. 15. In some embodiments, a diagnostic image can include tissue density, tissue state, identified disease tissue, or the like. The system 1402 can use the displayed data to perform one or more surgical steps. A user can view the display 1422 to confirm the position of the tissue during the procedure.

Figure 14C:
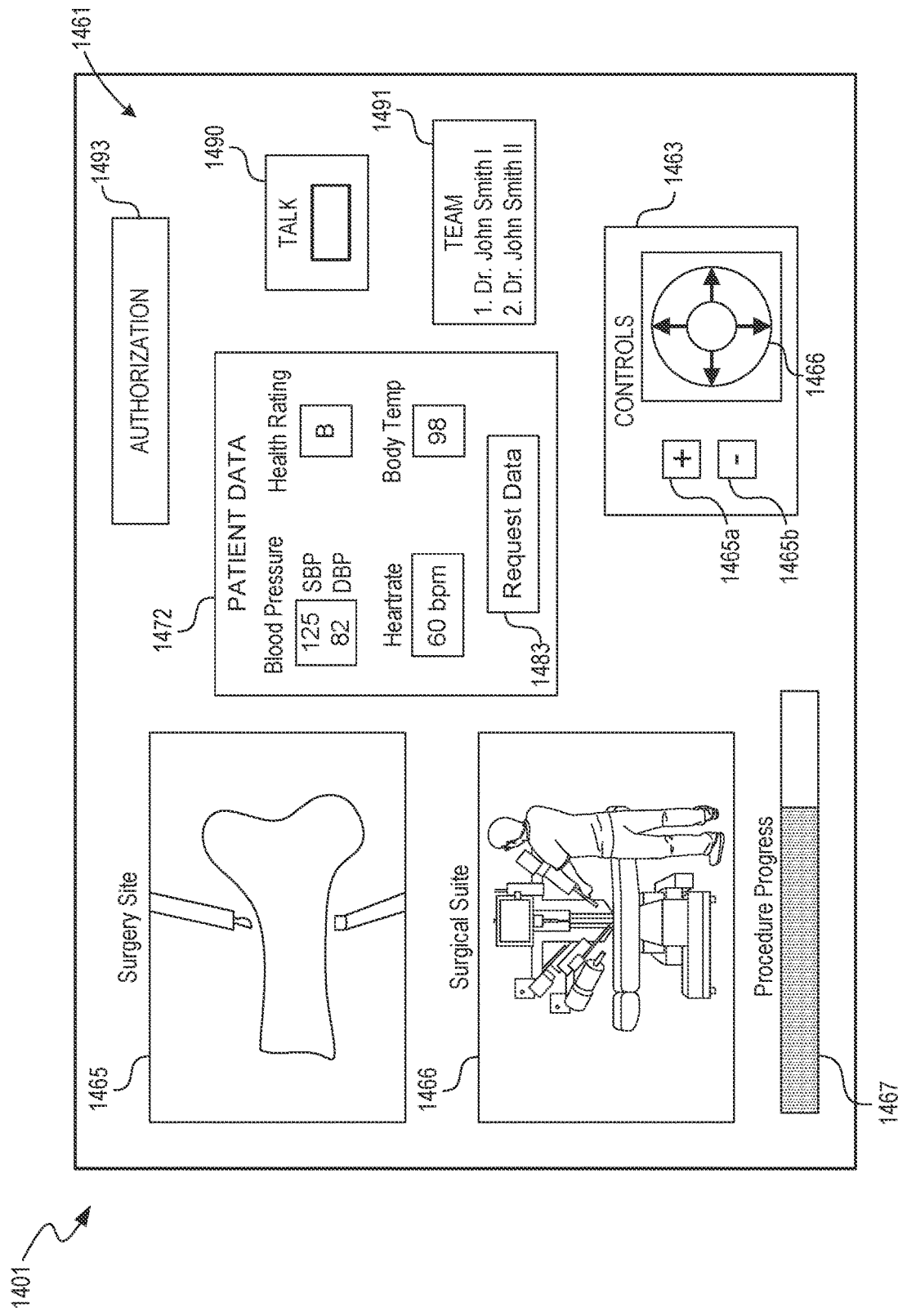
FIG. 14C illustrates an example display of a user device, in accordance with one or more embodiments.

Referring to FIGS. 14A and 14C, the consultant device 1401 can display procedure information from the surgery room, equipment controls, and other data disclosed herein. Referring now to FIG. 14C, the consultant device can display a graphical user interface ("GUI") 1461 for telepresence consulting. The GUI 1461 includes an authorization input 1493 for authorizing the consultant for participation in a surgical procedure and displays procedure and patient data 1465, 1466, 1472, 1491. Imaging equipment can automatically capture images for surgical side viewing via a display 1465. The GUI 1461 includes a procedure progress 1467 that can be updated to show completed progress for the procedure, and controls 1463 can be used to operate machines/applications. The user can customize the GUI 1461 by rearranging the displayed items for convenience.

The consultant can use an authorization input 1493 to, for example, input user authorization information (e.g., access codes, pins, etc.), employee credential information, surgical procedure information (e.g., serial number or code for the surgical procedure), or the like to access and operate equipment. If the consultant needs additional permission rights, the consultant can request the additional permission rights using the authorization input 1493. For example, if an adverse event occurs during the procedure requiring the consultant to provide additional care, the consultant can request access to the additional equipment (e.g., robotic arms of surgical robot, breathing machine, heart rate monitor, etc.) via the authorization input 1493. The surgical suite system can receive the requested authorization and perform an authorization protocol routine to determine whether the consultant should be granted permission rights to the additionally requested equipment. The surgical suite system can analyze the surgical plan, planned permission rights (e.g., plan of permission rights assigning permission rights to features or steps of the surgical plan), consultant credentials and/or expertise, and/or other information disclosed herein to determine whether to grant permissions. If requested permission rights are denied, the on-site medical team can be notified of the denied request and consultant input, recommendation, etc. If the request is granted, the system can automatically establish communication and control channels for displaying the additional information for the additional equipment via the consultant device 1401. The procedure progress 1467 can show completed progress for the modified procedure based on the additional equipment.

Dynamic updating of the equipment controls 1463 on the consultant device 1401 allows the user to acquire control of additional medical equipment in the same consulting session without disrupting communication channels. This reduces the risk of latency and/or network problems that could affect the medical procedure. The controls 1463 can be configured to perform all or some of the controls as discussed in connection with FIG. 14B. For example, the controls 1463 can include a touch input control module 1466 with input features 1465*a*, 1465*b* that can be used to increase or decrease, respectively, settings of equipment. The touch input control module 1466 can be used to control movement of, for example, robotic surgical arms, robotic manipulators, and effectors, or the like. For example, the touch input control module 1466 can be configured to provide the same controllability as the hand-operated input devices 1424, 1426 of FIG. 14B. In some embodiments, the controls 1463 of FIG. 14C can be modified to include controls for the additional equipment such that the consultant has access to controls for operating newly available equipment in real-time while continuing to view real-time patient data 1472. Data collected by and/or associated with additional equipment can automatically be added to the patient data 1472.

The consultant device 1401 can include a procedure viewer 1465, a surgical suite or room viewer 1466, and/or other viewers or windows for providing viewing (e.g., real-time or near real-time viewing) of the surgical suite (e.g., viewing at operating rooms, recovery rooms, etc.), medical team, medical equipment, etc. The consultant device 1401 can display patient data 1472 that can include, for example, blood pressure, health rating, heart rate, body temperature, vitals, physician notes, and/or additional patient data useful to the consultant. To change or receive additional patient data, the consultant can use a request data button 1483 to send a message or notification to the on-site surgical team to provide additional patient data. The consultant can use a talk feature 1490 to verbally communicate with the surgical team. The consultant device 1401 can also display the surgical team information 1491. The surgical team information can list physicians, nurses, staff, consultants, and other staffing information.

The robotic surgical system 1400, illustrated and described in more detail with reference to FIG. 14A, can further include multiple consultant devices 1401 so that multiple members of a surgical team or consultants can view the surgical procedure. The number and configuration of the consultant devices 1401 can be selected based on the configuration and number of surgical robots, monitoring equipment, etc. The consultant device 1401 can also display procedure data, including a surgical plan (e.g., a surgical plan including completed and future planned surgical steps), patient monitor readings, surgical suite or room information (e.g., available team members, available surgical equipment, surgical robot status, or the like), images (e.g., pre-operative images, images from simulations, real-time images, instructional images, etc.), and other surgical assist information. In some embodiments, the consultant device 1401 can be an AR/VR headset, display, or the like.

Referring to FIG. 14A, the robotic surgical system 1400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 1400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 15:
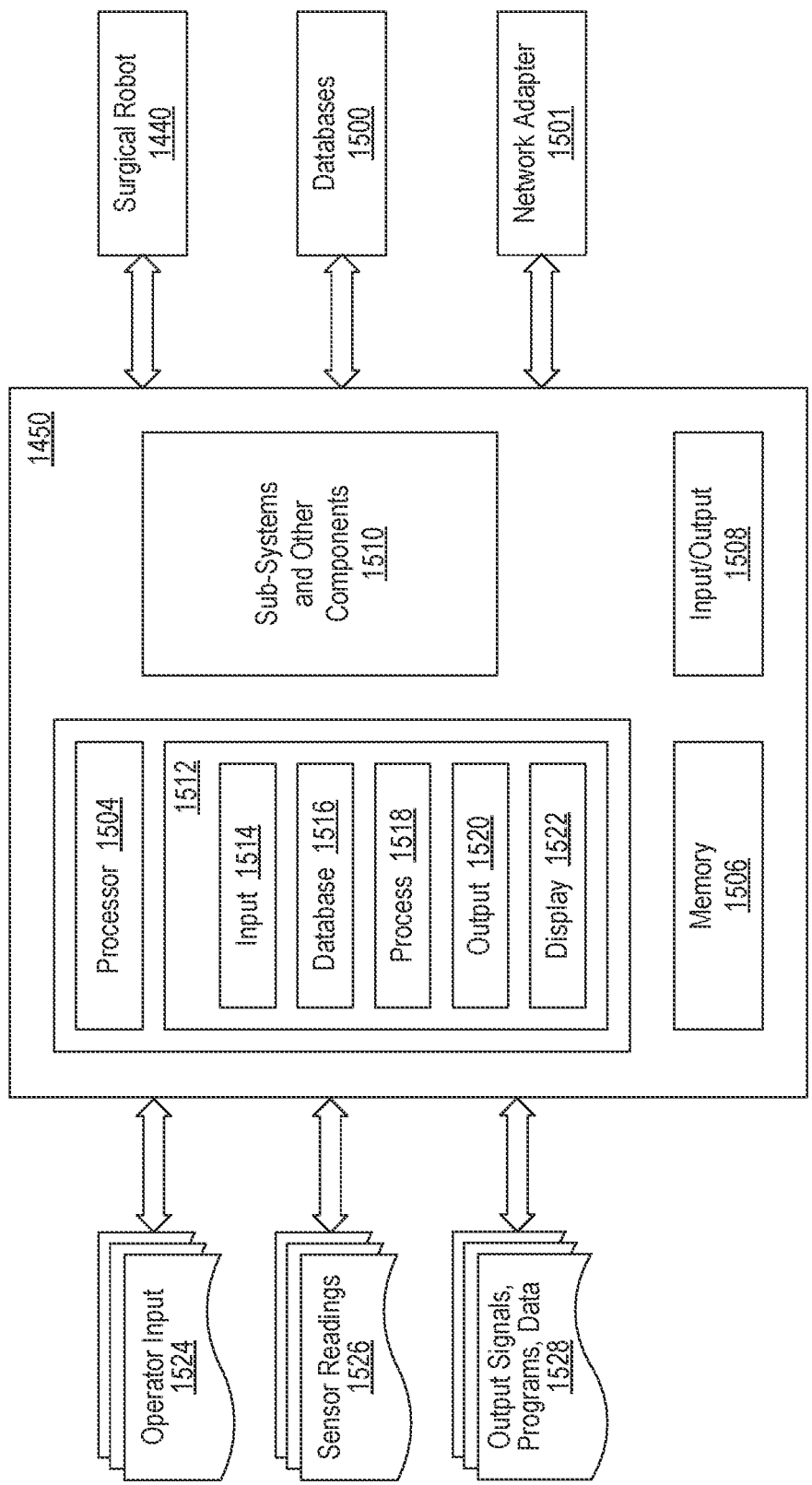
FIG. 15 is a schematic block diagram illustrating subcomponents of the robotic surgical system of FIG. 14A, in accordance with one or more embodiments.

FIG. 15 is a schematic block diagram illustrating subcomponents of the robotic surgical system 1400 of FIG. 14A in accordance with embodiment of the present technology. The controller or data system 1450 has one or more processors 1504, a memory 1506, input/output devices 1508, and/or subsystems and other components 1510. The processor 1504 can perform any of a wide variety of computing processing, image processing, robotic system control, plan generation or modification, and/or other functions. Components of the data system 1450 can be housed in a single unit (e.g., within a hospital or surgical room) or distributed over multiple, interconnected units (e.g., though a communications network). The components of the data system 1450 can accordingly include local and/or devices.

As illustrated in FIG. 15, the processor 1504 can include a plurality of functional modules 1512, such as software modules, for execution by the processor 1504. The various implementations of source code (i.e., in a conventional programming language) can be stored on a computer-readable storage medium or can be embodied on a transmission medium in a carrier wave. The modules 1512 of the processor 1504 can include an input module 1514, a database module 1516, a process module 1518, an output module 1520, and, optionally, a display module 1524 for controlling the display.

In operation, the input module 1514 accepts an operator input 1524 via the one or more input devices (including consultant devices), and communicates the accepted information or selections to other components for further processing. The database module 1516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 1506, external databases, etc.). Any type of database organization can be utilized, including a flat file system, hierarchical database, relational database, distributed database, etc.

In the illustrated example, the process module 1518 can generate control variables based on sensor readings 1526 from sensors (e.g., end effector sensors of the surgical robot 1440, patient monitoring equipment, etc.), operator input 1524 (e.g., input from the surgeon console 1420 and/or other data sources), and the output module 1520 can communicate operator input to external computing devices and control variables to controllers. The display module 1522 can be configured to convert and transmit processing parameters, sensor readings 1526, output signals 1528, input data, treatment profiles and prescribed operational parameters through one or more connected display devices, such as a display screen, touchscreen, printer, speaker system, etc.

In various embodiments, the processor 1504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 1506 can be standard memory, secure memory, or a combination of both memory types. By employing a secure processor and/or secure memory, the system can ensure that data and instructions are both highly secure and sensitive operations such as decryption are shielded from observation. In various embodiments, the memory 1506 can be flash memory, secure serial EEPROM, secure field-programmable gate array, or secure application-specific integrated circuit. The memory 1506 can store instructions for causing the surgical robot 1440 to perform acts disclosed herein.

The input/output device 1508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 1508 can alert the subject and/or operator via an audible alarm. The input/output device 1508 can be a touch screen that functions as both an input device and an output device.

The data system 1450 can output instructions to command the surgical robot 1440 and communicate with one or more databases 2600. The surgical robot 1440 or other components disclosed herein can communicate to send collected data (e.g., sensor readings, instrument data, surgical robot data, etc.) to the database 1500. This information can be used to, for example, create new training data sets, generate plans, perform future simulations, post-operatively analyze surgical procedures, or the like. The data system 1450 can be incorporated, used with, or otherwise interact with other databases, systems, and components disclosed herein. In some embodiments, the data system 1450 can be incorporated into the surgical robot 1440 or other systems disclosed herein. In some embodiments, the data system 1450 can be located at a remote location and can communicate with a surgical robot via one or more networks. For example, the data system 1450 can communicate with a hospital via a network, such as a wide area network, a cellular network, etc. One or more local networks at the hospital can establish communication channels between pieces of surgical equipment within the surgical room. A network adapter 1501 can be an operator authorizing device to manage communications and operation of components, as described with reference to FIG. 3. The network adapter 1501 can govern and/or manage permissions to access proxy data in a computer network, track varying levels of trust between different machines and/or applications, and manage control access to surgical equipment, communications between remote devices and the surgical room, etc.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 1440. For example, mode switching programs can include threshold or configuration settings for determining when to switch the mode of operation of the surgical robot 1440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 16:
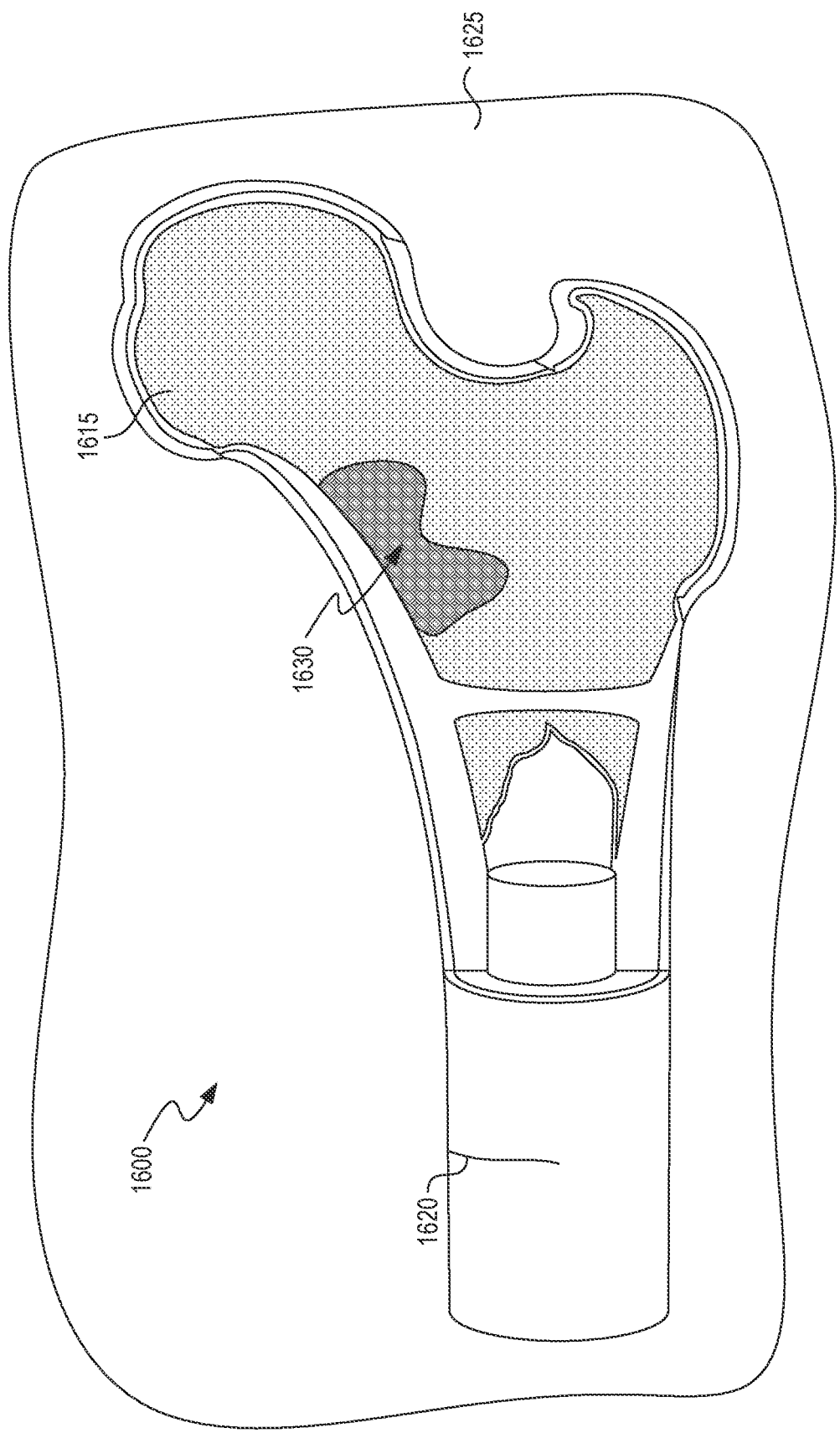
FIG. 16 illustrates an example multi-modality image of a target region, in accordance with one or more embodiments.

FIG. 16 illustrates an example of an image 1600, in accordance with one or more embodiments. The image 1600 can allow a healthcare worker to view a target region 1625 to analyze an automated diagnosis, anatomical features, identify tissue of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 1600 (e.g., a pre-operative image, real-time intra-operative image, etc.). The multi-modality image 1600 can be generated based on a surgical plan, physician input, or other input data, and can indicate features (e.g., anatomical elements), margins, tissue type, etc.

To generate the image 1600, systems disclosed herein can receive a tissue density image from an MRI device, a bone fracture image from a CT scanner, a bone degeneration or cancerous tissue image from an ultrasound machine, or images from other imagers disclosed herein. In embodiments, the image 1600 is generated for a surgical plan for treating a damaged bone and can include, for example, tissue density data 1615 (e.g., healthy tissue data from an MRI device), a bone fracture 1620 (e.g., identified using a CT scan), diseased tissue 1630 (e.g., low-density tissue, cancerous tissue, etc., from ultrasound images), or the like. The system can combine the data to generate the image 1600 with features and/or information of interest. In some embodiments, the image 1600 highlights regions 1625 of a tissue sample according to the diagnoses and/or the values from a multi-modality device or multiple imaging devices. For example, the image 1600 can annotate highlight and/or otherwise identify/emphasize features of interest. The emphasis can help direct the doctor's review of the target region 1625 and/or further analysis of the patient. In embodiments, images are generated that include raw data and multi-modality images (e.g., composite images, a multi-layer overlaid image, etc.) to allow a physician to perform an independent diagnosis. In embodiments, the raw data is indicated via differences in shading, color, fill patterns, express indications, display tables, selectable displays, and/or in any other suitable manner.

The multi-modality images can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer, surgical plan (e.g., features of interest, anatomical elements, etc.). For example, the image 1600 of FIG. 16 can include selectable layers each with one or more anatomical features identified (e.g., via annotation, false colors, etc.).

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments. This application is related to U.S. Ser. No. 17/865,342 and U.S. patent application Ser. No. 17/408,407, filed Aug. 21, 2021, entitled TELEPRESENCE-BASED SURGICAL CONSULTING, which are incorporated herein by reference in their entireties.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

What is claimed is:

1. A robotic surgery system comprising:
   a plurality of motorized robotic arms of a surgical robot configured to perform surgical steps on a patient;
   a display system for multi-user control of the surgical robot during a surgical procedure for the patient, the display system including
   a console including left and right hand-operated input devices physically manipulatable by a first user and a viewer configured to display one or more instruments carried by the plurality of robotic arms to the first user controlling motorized actuation of the surgical robot, and a second user device configured to display a graphical user interface having patient data of the patient and an authorization input for a second user to be authorized to switch control of at least one of the robotic arms from the first user to the second user to perform one or more surgical actions under control of the second user while the second user device real-time displaying of tissue at the surgical site of the patient.

2. The robotic surgery system of claim 1, further comprising a tissue imager configured to acquire low-density tissue and/or cancerous tissue at the surgical site using ultrasound or computed tomography imaging.

3. The robotic surgery system of claim 1, wherein the surgical robot is configured to translate manipulation of the left and right hand-operated input devices to first robotic arm movement and to translate second user input from controls of the graphical user interface to second robotic arms movement, wherein the left and right hand-operated input devices include a joystick and/or a hand-held controller.

4. The robotic surgery system of claim 1, further comprising at least one imaging device carried by at least one plurality of robotic arms configured to position the least one imaging device for viewing the surgical site independently of other robotic arms.

5. The robotic surgery system of claim 4, wherein the at least one imaging device is configured to capture image data transmitted to the second user device for viewing by the second user to remotely control one or more plurality of robotic arms based on permissions granted to the second user.

6. The robotic surgery system of claim 1, further comprising a patient monitor in communication with the second user device, wherein the patient monitor includes at least one of an end tidal CO2 monitor;
a capnography monitor;
a blood pressure monitor;
a body temperature monitor; or
a respiration rate monitor.

7. The robotic surgery system of claim 1, wherein the second user device displays:

control inputs for adjusting operation of medical equipment;
patient vitals; and
one or more images captured showing the surgical site.

8. A robotic surgical system-implemented method comprising:

determining, by a robotic surgery system, one or more surgical actions of a portion of a surgical procedure to be performed on a patient by one or more robotic arms of a surgical robot under control of a user of a plurality of users, establishing, by a computer system, at least one medical equipment operation channel for the portion of the surgical procedure to send procedure and patient data from a surgical suite to a user device at a remote location to cause the procedure and patient data to be displayed by the user device to the user;

authorizing, by an operator authorizing device, operation of the medical equipment by the user for the one or more surgical actions of the surgical procedure performed on the patient at the surgical suite, wherein the authorization is based on a surgical procedure plan and a stored access control list that includes permissions for the user;

determining, using a machine learning module of the computer system, that the one or more surgical actions of the surgical procedure has been completed, wherein the machine learning module compares historical images to the one or more images of the patient to determine whether one or more surgical actions have been completed; and responsive to determining that the one or more surgical actions of the surgical procedure has been completed,
terminating, by the computer system, the at least one medical equipment operation channel, and
switching control of the one or more robotic arms to a different user of the plurality of users to perform one or more additional surgical actions of a second portion of a surgical procedure.

\* \* \* \* \*